US011414641B2

(12) United States Patent
Chandrapati et al.

(10) Patent No.: US 11,414,641 B2
(45) Date of Patent: Aug. 16, 2022

(54) ARTICLE AND METHOD FOR DETECTING AEROBIC BACTERIA

(71) Applicant: 3M INNOVATIVE PROPERTIES COMPANY, St. Paul, MN (US)

(72) Inventors: Sailaja Chandrapati, Woodbury, MN (US); Tera M. Nordby, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/117,348

(22) Filed: Dec. 10, 2020

(65) Prior Publication Data

US 2021/0087516 A1    Mar. 25, 2021

Related U.S. Application Data

(62) Division of application No. 15/123,272, filed as application No. PCT/US2015/018844 on Mar. 5, 2015, now abandoned.

(60) Provisional application No. 61/949,631, filed on Mar. 7, 2014.

(51) Int. Cl.
*C12Q 1/04*    (2006.01)
*C12M 1/34*    (2006.01)

(52) U.S. Cl.
CPC ............ *C12M 41/36* (2013.01); *C12Q 1/04* (2013.01); *C12Q 2334/52* (2013.01)

(58) Field of Classification Search
None
See application file for complete search history.

(56) References Cited

U.S. PATENT DOCUMENTS

| | | |
|---|---|---|
| 4,565,783 A | 1/1986 | Hansen et al. |
| 5,089,413 A | 2/1992 | Nelson et al. |
| 5,364,766 A | 11/1994 | Mach et al. |
| 5,448,652 A | 9/1995 | Vaidyanathan et al. |
| 5,601,998 A | 2/1997 | Mach et al. |
| 5,635,367 A | 6/1997 | Lund |
| 5,681,712 A | 10/1997 | Nelson |
| 5,854,011 A | 12/1998 | Chen et al. |
| 5,962,251 A | 10/1999 | Rambach |
| 6,058,209 A | 5/2000 | Vaidyanathan et al. |
| 6,090,541 A | 7/2000 | Wicks et al. |
| 6,243,486 B1 | 6/2001 | Weiss |
| 6,271,022 B1 | 8/2001 | Bochner |
| 6,387,650 B1 | 5/2002 | Townsend et al. |
| 7,141,387 B2 | 11/2006 | Ushiyama |
| 7,298,885 B2 | 11/2007 | Green et al. |
| 7,319,031 B2 | 1/2008 | Vent et al. |
| 8,415,115 B2 | 4/2013 | Orenga et al. |
| 8,420,345 B2 * | 4/2013 | Orenga .................. C12Q 1/04 435/34 |
| 8,753,834 B2 * | 6/2014 | Miller ..................... C12Q 1/06 435/34 |
| 8,828,682 B2 * | 9/2014 | Mach ...................... C12Q 1/04 435/39 |
| 8,921,067 B2 | 12/2014 | Chandrapati et al. |
| 2002/0086278 A1 | 7/2002 | Gosnell |
| 2006/0008867 A1 | 1/2006 | Ushiyama |

FOREIGN PATENT DOCUMENTS

| | | |
|---|---|---|
| WO | WO 91/11509 | 8/1991 |
| WO | WO 93/12218 | 6/1993 |
| WO | WO 95/29984 | 11/1995 |
| WO | WO 1998/45469 | 10/1998 |
| WO | WO 2010077619 | 7/2010 |
| WO | WO 2011/082305 | 7/2011 |
| WO | WO 2014/121243 | 8/2014 |

OTHER PUBLICATIONS

US 4,476,226 A, 10/1984, Hansen et al. (withdrawn)
Nollet, Leo M.L. (translated by Hongfu et al.), *Handbook of Water Analysis*, New York, China Petrochemical Press, Jun. 30, 2005, pp. 116-118.
Bascomb, S. et al.; "Use of Enzyme Tests in Characterization and Identification of Aerobic and Facultatively Anaerobic Gram-Positive Cocci"; Clinical Microbiology Reviews; vol. 11, No. 2; 1998; pp. 318-340.
BD Bionutrients™ Technical Manual, Advanced Bioprocessing, Third Edition Revised, Oct. 2006. Online: http://galachern.ru/upload/iblock/90S/bd_bionutrients_technical_man_3_2547.pdf—Accessed full pdf online on Jan. 2, 2020.
Brazil Search Report for BR112016020570-7 dated Oct. 21, 2019.
Csonka et al., J. Biol. Chem. 1935, 109: 703-15.
Dong, W.; "Screening of the Xanthan and Guar Gum Degrading Microbes"; The Excellent Chinese Mater's Theses Full-text Database; Engineering Science and Technology Series 1, Issue 4, B019-2; Apr. 15, 2009 (28 pgs).
Ferreira et al. Food Chemistry, 1997, vol. 60, No. 2, pp. 251-254.
Orenga S et al: "Enzymatic substrates in microbiology", Journal of Microbiological Methods, Elsevier, Amsterdam, NL, vol. 79, No. 2, Nov. 1, 2009 (Nov. 1, 2009), pp. 139-155.

(Continued)

*Primary Examiner* — Vera Afremova
(74) *Attorney, Agent, or Firm* — 3M IPC

(57) ABSTRACT

A thin film culture device for detecting aerobic bacteria in a sample is provided. The culture device comprises a self-supporting substrate sheet having a first major surface and a second major surface; a cover sheet attached to the substrate sheet, a sample-receiving zone disposed between the substrate sheet and the cover sheet, a first layer comprising a substantially dry, cold-water-soluble first hydrogel-forming composition adhered to a portion of the sample-receiving zone; and a plurality of indicator agents disposed in at least one layer adhered to the substrate sheet or the cover sheet. The plurality of indicator agents comprises three indicator agents for detecting distinct glycosidase enzyme activities, an indicator agent for detecting an alkyl esterase enzyme activity, an indicator agent for detecting a phosphatase enzyme activity, and a redox indicator. A method of using the culture device is also provided.

4 Claims, 2 Drawing Sheets

(56) References Cited

OTHER PUBLICATIONS

Slots, J.; "Enzymatic Characterization of Some Oral and Nonoral Gram-Negative Bacteria with the API ZYM System"; Journal of Clinical Microbiology; vol. 14, No. 3; 1981; pp. 288-294.
Zhou et al., "Basic Operation Guide for Analyzing Preparations Made from Hospitals," Jan. 31, 2012, *People's Military Medical Press*, pp. 130-132.

* cited by examiner

ARTICLE AND METHOD FOR DETECTING AEROBIC BACTERIA

CROSS REFERENCE TO RELATED APPLICATIONS

This application is a divisional of U.S. patent application Ser. No. 15/123,272, filed Sep. 2, 2016, which is a national stage filing under 35 U.S.C. 371 of PCT/US2015/018844, filed Mar. 5, 2015, which claims the benefit of U.S. Provisional Patent Application No. 61/949,631, filed Mar. 7, 2014, the disclosures of which are incorporated by reference in their entireties herein.

BACKGROUND

The aerobic plate count (APC) is used as an indicator of total microbial load in a sample (e.g., a sample of a food). Conventionally, an APC is performed using pour-plate methods, surface-spread methods, spiral plate count methods, or membrane filtration methods; all of which typically utilize agar culture media to grow and enumerate the microorganisms.

Media for culturing bacteria are generally prepared by dispersing a solidifying agent in an aqueous solution containing nutrients and other ingredients necessary for the growth of specific microorganisms. Unfortunately, use of conventional solidifying agents is often inconvenient for the end-user. For example, when carrying out standard "plate count" or "pour plate" methods to determine the number of microorganisms in a liquid sample such as water or milk, the use of conventional agar medium is particularly inconvenient and time consuming. The agar medium, which generally is prepared in bulk and sterilized ahead of time, is melted in boiling water or by exposure to flowing steam. The hot agar is then carefully cooled to approximately 45° C. prior to pouring into petri dishes. A series of dilutions of the test sample is then prepared and an aliquot of each dilution is placed in a petri dish. The cooled, but still liquefied, agar medium is then poured into each dish, mixed with the aliquot of test sample, swirled to mix and allowed to solidify. After incubation, the number of colonies growing in each dish is counted by visual inspection. In this manner the number of microorganisms or colony-forming units present in the test sample can be determined.

Most importantly, most of the conventional methods for enumerating aerobic bacteria require an incubation period of at least 48 hours before accurate quantitative results can be obtained. The long incubation period of these methods can require that food products be stored for several days, until the presence or concentration of contaminating aerobic bacteria is finally known.

Thin film culture devices are also available to grow and enumerate aerobic bacteria. U.S. Pat. Nos. 4,565,783 and 5,681,712; which are incorporated herein by reference in their entirety; disclose devices for culturing and enumerating aerobic bacteria.

Thus, there is a need for improved tests and related materials. If the test procedures could be simplified, and test results obtained in a shorter period of time, it would allow manufacturers to release products; thereby reducing storage costs without sacrificing product quality and integrity.

SUMMARY

The present disclosure generally relates to a device for culturing and detecting microorganisms. In addition, the present disclosure relates to a method for culturing and detecting microorganisms in a sample. In particular, the present disclosure relates to rapid detection of aerobic and aero-tolerant bacteria in a dry, reconstitutable culture device comprising a plurality of indicator agents disposed at high concentrations in an adhesive composition. The plurality of indicator agents include an indicator agent for detecting an alkyl esterase enzyme activity, an indicator agent for detecting a phosphatase enzyme activity, three indicator agents for detecting distinct glycosidase enzyme activities, and a redox indicator. Advantageously, the plurality of indicator agents permits rapid detection and enumeration of a wide variety of aerobic bacteria. Even more advantageously, the specific indicator agents, together with the concentrations thereof and the means for providing the indicator agents to the microorganisms, permit the detection and enumeration of the aerobic and/or aerotolerant bacteria in about 48 hours or less and, preferably, in about 26 hours or less.

In one aspect, the present disclosure provides a device for culturing and detecting microorganisms. The device can comprise a self-supporting substrate sheet having a first major surface and a second major surface; a cover sheet attached thereto; a sample-receiving zone disposed between the substrate sheet and the cover sheet; a first layer comprising a substantially dry, cold-water-soluble first hydrogel-forming composition adhered to the first major surface of the substrate sheet; and a plurality of indicator agents. The plurality of indicator agents can comprise three enzyme activity indicator reagents for detecting distinct glycosidase enzyme activities, an enzyme activity indicator reagent for detecting an alkyl esterase enzyme activity, an enzyme activity indicator reagent for detecting a phosphatase enzyme activity, and a redox indicator. Each of the plurality of enzyme activity indicator reagents can comprise a detectable reporter group. Each of the plurality of indicator agents can be disposed in at least one layer adhered to the substrate sheet or the cover sheet, wherein the at least one layer is in fluid communication with the sample-receiving zone when a predetermined volume of aqueous liquid is deposited in the sample-receiving zone.

In any of the above embodiments, the redox indicator can comprise a tetrazolium dye. In any of the above embodiments, the tetrazolium dye can comprise triphenyltetrazolium chloride. In any of the above embodiments, the device further can comprise a second layer comprising a first adhesive composition disposed between the substrate sheet and the first layer, wherein the device optionally can comprise an air-permeable membrane adhered to the substrate sheet. In any of the above embodiments, the device further can comprise a water-insoluble spacer having an aperture, the spacer being attached to the substrate sheet or the cover sheet and the aperture being positioned between the substrate sheet and the cover sheet, wherein the aperture defines a peripheral boundary of the sample-receiving zone.

In another aspect, the present disclosure provides a method of detecting an aerobic bacterium in a sample. The method can comprise contacting a sample material and an aqueous liquid in the sample-receiving zone of the device of any one of the above embodiments to form an inoculated culture device, incubating the inoculated culture device for a period of time, and detecting a bacterial colony in the culture device. In any embodiment of the method, detecting a bacterial colony in the culture device can comprise detecting in the culture device a presence of a formazan dye or the detectable reporter group of at least one of the indicator agents, wherein detecting the presence of the formazan dye or the detectable reporter group is indicative of a presence of a colony of bacteria.

The term "powder", as used herein, refers to particulate material of one or more gelling agents or nutrients having an average diameter suitable for use in the thin film culture device(s) of the present invention, preferably a diameter of about 10-400 microns more preferably a diameter of about 30-90 microns.

As used herein, "reconstituted medium" refers to a solution or gel formed from the reconstitution of a cold-water-soluble powder with an aqueous liquid.

The term "cold-water-soluble powder", as used herein, refers to a powder that forms a gel in room temperature water (e.g., about 18° C. to 24° C.) when combined with an aqueous test sample.

The term "substantially impermeable to microorganisms and water vapor", as used herein, refers to a cover sheet that prevents undesired contamination and hydration of underlying layers of cold-water-soluble powder during shipping, storage, and use of thin film culture device(s), and avoids desiccation of the reconstituted medium, such that the reconstituted medium is suitable to support the growth of microorganisms during an incubation period.

The term "aerobic bacterium", as used herein, refers to a typically-unicellular, prokaryotic microorganism that is capable of utilizing molecular oxygen as a terminal oxidizing agent in aerobic respiration to produce energy for cellular processes (e.g., metabolism, biosynthesis, replication). Aerobic bacteria include facultative anaerobic bacteria that, in addition to being capable of utilizing molecular oxygen as a terminal oxidizing agent, are also capable of energy production via fermentation. Aerobic bacteria include one or more species that exist or co-exist collectively in a test sample. The term "aerobic bacteria" also refers to the array of aerobic bacteria found, e.g., in a test sample. The term "aerobic bacteria" is not limited to mean any given number of these microorganisms or species and is not meant to exclude species which have yet to be discovered but may later be identified and included in this definition by those of skill in the art.

The term "test sample", as used herein, refers to a component or portion taken from a food product, a human or animal test subject, pharmaceutical or cosmetic commodity, soil, water, air or other environmental source, or any other source from which a presence and, optionally, an enumeration of aerobic and/or aerotolerant bacteria is to be determined. A test sample may be taken from a source using techniques known to one skilled in the art including, for example, pouring, pipetting, swabbing, filtering, and contacting. In addition, the test sample may be subjected to various sample preparation processes known in the art including, for example, blending, stomaching, homogenization, enrichment, selective enrichment, or dilution.

The term "substantially water-free", as used herein, designates a water content no greater than about the water content of the ambient environment.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a culture device comprising "an" indicator agent can be interpreted to mean that the culture device can comprise "one or more" indicator agents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

DETAILED DESCRIPTION

Figure 1:
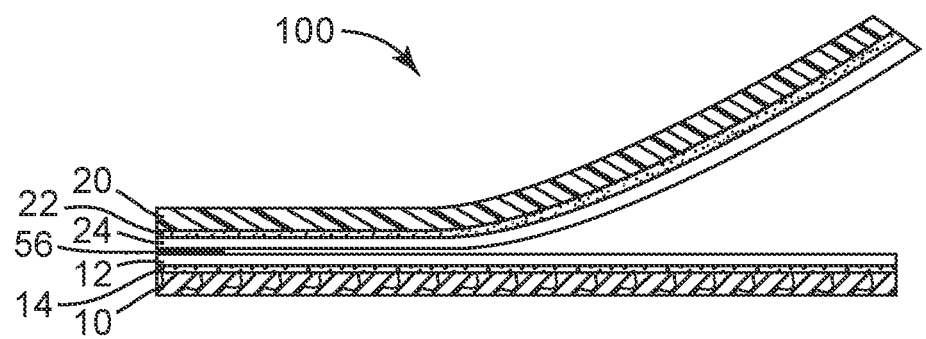
FIG. 1 is a schematic cross-sectional side view of one embodiment of a culture device of the present disclosure, wherein certain features are shown.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Aerobic bacteria are ubiquitous microorganisms, some of which have a significant role in the spoilage of food and beverages. The number of aerobic bacteria in a sample (e.g., a food sample, a water sample, or environmental surface sample) may be an indication of the possible presence of pathogenic microorganisms in the food, water, or environment. Moreover, the number of total aerobic bacteria in food or beverage samples can be an indicator of the remaining shelf life for the food or beverage from which the sample came. Therefore, it is routine for most food and beverage producers to monitor their products and/or processing environment for the presence and quantity of aerobic bacteria.

Traditional testing for aerobic bacteria typically involves culturing the microorganisms on agar media or in thin-film culture devices such as a 3M PETRIFILM Aerobic Count Plate (available from 3M Company, St. Paul, Minn.). Thin film culture devices for detecting yeast and mold in a sample are described, for example, in U.S. Pat. No. 4,565,783. The traditional testing methods involve incubating the test plates for a period of at least 2 days to get accurate counts. The period it takes to complete the testing for aerobic bacteria can cause food processors to hold the food product for at least about 2-3 days in order to determine whether the food product contains a large enough quantity of aerobic bacteria that may adversely affect the quality and/or safety of the food product during normal conditions of storage and use.

Some culture media, including the culture medium used in 3M PETRIFILM Aerobic Count plates, include at least one indicator reagent (e.g., triphenyltetrazolium chloride) that is converted by aerobic bacteria to a detectable (e.g., detectable by light absorption, reflectance, and or fluorescence) product (e.g., formazan). U.S. Pat. No. 6,387,650 granted to Townsend and Chen; which is incorporated herein by reference in its entirety; discloses compositions for detecting bacteria in a test sample, wherein the compositions comprise three enzyme substrates that cause or produce an identical type of detectable signal (e.g., fluorescence) when hydrolyzed by a corresponding enzyme activity found in the bacteria. One enzyme substrate is hydrolyzed by a glycosidase enzyme activity, a second enzyme substrate is hydrolyzed by a peptidase enzyme activity and the third enzyme substrate is hydrolyzed by a phosphatase enzyme activity. In the patent, Townsend and Chen further describe the use of media containing the indicator reagents in a culture device that permits the calculation of a most probable number (MPN) of microorganisms in the test sample.

In one aspect, the present disclosure provides a culture device for detecting aerobic and/or aerotolerant bacteria in a sample. The components of the culture device, when contacted with an aqueous liquid, can act cooperatively to form an aqueous culture medium that is used to cultivate and optionally quantitate aerobic and/or aerotolerant bacteria in a sample. In any embodiment, the culture medium of the present disclosure can be a mixture which comprises all or substantially all of the nutrients necessary to support the growth of aerobic or aerotolerant bacteria. In some embodiments, one or more nutrients to support the growth of aerobic or aerotolerant bacteria may be provided in the sample.

The culture device of the present disclosure provides improved detection (i.e., reduced time to detection, more inclusive detection of aerobic and/or aerotolerant bacteria within a specified incubation period) compared to other devices and methods known in the art. In some aspects, a culture device of the present disclosure is related to thin film culture devices disclosed in U.S. Pat. Nos. 4,565,783; 5,089,413; and 5,681,712; which are all incorporated herein by reference in their entirety.

Suitable samples for use with the inventive culture device can be obtained or derived from a variety of sources. The term "source" is generally used to refer to the food or nonfood desired to be tested for aerobic and aerotolerant bacteria. The source can be a solid, a liquid, a semi-solid, a gelatinous material, gas (e.g., air), and combinations thereof. In some embodiments, the source can be provided by a capture element (e.g., a filter membrane, swab, fabric, or sponge) that was used, for example, to collect the source from a surface of interest or from air. In some embodiments, a sample liquid can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

Figure 2:
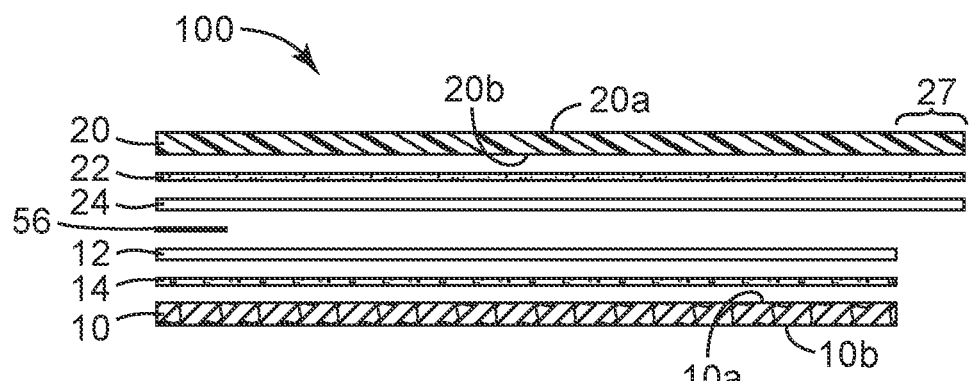
FIG. 2 is an exploded schematic cross-sectional side view of the culture device of FIG. 1.

With reference to FIGS. 1-2, a device 100 of the present disclosure comprises a waterproof substrate sheet 10, a cover sheet 20, and a first layer 12 comprising a substantially dry, cold-water-soluble first hydrogel-forming composition. The substrate sheet 10 has a first major surface 10a and a second major surface 10b opposite the first major surface. Although the substrate sheet 10, cover sheet 20, and first layer 12 can be arranged in any suitable relationship; FIG. 1 illustrates a preferred arrangement of these components, wherein first layer 12 is adhered to and covers at least a portion of a sample-receiving zone 30. In any embodiment, an optional second layer 14 can be disposed between the substrate sheet 10 and the first layer 12. In any embodiment, the second layer can comprise a first adhesive composition. In any embodiment, the device 100 further comprises an optional spacer 50. The spacer 50 comprises an aperture 52 that defines a perimeter of the sample-receiving zone 30.

The sample-receiving zone 30 occupies an area between the substrate sheet 10 and the cover sheet 20. The area can be regular-shaped or irregular-shaped. In any embodiment, the volume can be defined by the aperture 52 of a spacer 50. The aperture 52 can be any shape. Non-limiting examples of useful shapes for the sample-receiving zone 30 (or aperture 52) include a square, a rectangle, a circle, an oval, a polygon, a hexagon, and an octagon.

The area of the sample-receiving zone may be selected based on, for example, the volume of aqueous liquid to be deposited in the zone. In any embodiment, for a 0.5-3 milliliter volume of aqueous liquid, the area of the sample-receiving zone is about 10 cm$^2$. In any embodiment, for a 0.5-3 milliliter volume of aqueous liquid, the area of the sample-receiving zone is about 15 cm$^2$. In any embodiment, for a 1-5 milliliter volume of aqueous liquid, the area of the sample-receiving zone is about 20 cm$^2$. In any embodiment, for a 1-5 milliliter volume of aqueous liquid, the area of the sample-receiving zone is about 25 cm$^2$. In any embodiment, for a 1-5 milliliter volume of aqueous liquid, the area of the sample-receiving zone is about 30 cm$^2$. In any embodiment, for a 1-5 milliliter volume of aqueous liquid, the area of the sample-receiving zone is about 31 cm$^2$. In any embodiment, for a 1-5 milliliter volume of aqueous liquid, the sample receiving zone is about 25-35 cm$^2$.

First layer 12 is fixed to a portion of the substrate sheet 10 and/or a portion of the second layer 14, if present. The first layer 12 covers at least a portion of the sample-receiving zone 30 of the device 100. Cover sheet 20 for covering the first layer 12 during shipping, storage, and incubation, is also shown in FIGS. 1 and 2 as being attached in a hinge-like fashion along one edge of the spacer 50. The cover sheet 20 can be attached by any suitable means including, for example, a double-sided adhesive tape 56, as shown in FIG. 2. Suitable substrate sheets 10, components of the first hydrogel-forming composition, and cover sheets 20 include those described in U.S. Pat. No. 4,565,783, which is incorporated herein by reference in its entirety. At least a portion of the first layer 12 is in fluidic communication with the sample-receiving zone 30 after the device 100 is hydrated with a predetermined quantity of an aqueous liquid.

Substrate sheet 10 can be a relatively stiff film (e.g., polyester, polypropylene or polystyrene) or a relatively stiff paper or cardboard having a water-resistant coating thereon, which will not absorb or otherwise be affected by water. Polyester films approximately 100 µm, to 180 µm, thick, polypropylene films approximately 100 µm, to 200 µm, thick, and polystyrene films approximately 300 µm, to 380 µm thick are nonlimiting examples of suitable materials for the substrate sheet 10. The substrate sheet 10 may be either transparent or opaque, depending on whether one wishes to view microorganism colonies through the substrate sheet. To facilitate the counting of microorganism colonies, the substrate sheet 10 optionally can have a grid pattern (e.g., squares, not shown) printed thereon.

The first adhesive composition in the second layer 14 is preferably pressure-sensitive, insoluble in water, and substantially non-inhibitory to the growth of the intended microorganisms, as described in U.S. Pat. No. 4,565,783. In any embodiment, the second layer can be coated onto a suitable substrate sheet (e.g., using a knife coater). Preferably, the first adhesive composition is substantially transparent when wet to enable viewing of microbial colonies. At least a portion of the second layer 14 is in fluidic communication with the sample-receiving zone 30 after the device 100 is hydrated with a predetermined quantity of an aqueous liquid.

Referring back to FIGS. 1-2, adhered to at least a portion (e.g., in at least a part of the sample-receiving zone 30) of the substrate sheet 10, either directly or indirectly, is the first layer 12. The first layer 12 comprises a first substantially water-free, cold-water-soluble first hydrogel-forming composition. In any embodiment, a portion or the entirety of the first layer 12 can be adhered directly to the substrate sheet 10 (e.g., the first side 10a of the substrate sheet 10). In any embodiment, a portion or the entirety of the first layer 12 can be adhered to the second layer 14, if present. The first hydrogel-forming composition can be dissolved and/or suspended in an aqueous liquid (e.g., deionized water) and coated onto the substrate sheet 10, after which it can be dried until it is substantially water-free, as described in U.S. Pat. No. 4,565,783, for example.

The first hydrogel-forming composition of the first layer 12 comprises at least one cold water soluble gelling agent. As indicated above, the first composition can contain gelling agent only, and no nutrient. Optionally, in any embodiment, the first hydrogel-forming composition also may comprise an effective amount of a nutrient to facilitate growth of aerobic bacteria and/or aerotolerant bacteria.

Suitable gelling agents for use in first hydrogel-forming composition include cold-water-soluble natural and synthetic gelling agents. Non-limiting examples of suitable natural gelling agents include align, carboxymethyl cellulose, hydroxyethyl cellulose, locust bean gum, xanthan gum. Suitable synthetic gelling agents include, for example polyacrylamide. Combinations of natural and/or synthetic gelling agents are contemplated. Preferred gelling agents include guar gum, xanthan gum, and locust bean gum, these gelling agents being useful individually or, in any embodiment, in combination with one another. A uniform monolayer of cold-water-soluble first hydrogel-forming composition and/or second hydrogel-forming composition is desired with sufficient surface area exposed for hydration. In any embodiment, the first and/or second hydrogel-forming composition comprises a mixture of gelling agents. In any embodiment, the mixture comprises guar gum and xanthan gum. In any embodiment, the mixture may comprise guar gum and xanthan gum in a mass ratio of about 1:1. Surprisingly, a gelling agent mixture comprising a 1:1 mass ratio of guar gum to xanthan gum substantially resists liquefaction by certain microorganisms (e.g., certain *Bacillus* species) that produce an enzyme that liquefies (i.e., hydrolyzes) guar gum.

The first hydrogel-forming composition of the first layer 12, preferably, includes a cold water-soluble gelling agent in an amount such that a predetermined quantity of water or an aqueous sample, e.g., 1 to 3 ml, placed in the sample-receiving zone 30 will form a hydrogel having a suitable viscosity, e.g., about 1500 cps or more when measured at 60 rpm with a Brookfield Model L VF viscometer at 25° C. Hydrogels of this viscosity allow convenient handling and stacking of the culture devices 100 during incubation and provide for distinct colony formation in the hydrogel. For instance, 0.025 g to 0.050 g of powdered guar gum spread substantially uniformly over a surface area of 20.3 cm$^2$ will provide a sufficiently viscous medium when reconstituted with 1 to 3 ml of an aqueous sample. Suitable amounts of gelling agent (e.g., guar gum) per unit area of the sample-receiving zone are discussed in U.S. Pat. No. 5,089,413, for example.

In any embodiment, the first hydrogel-forming composition further includes at least one nutrient to facilitate growth of aerobic bacteria and/or aerotolerant bacteria. In any embodiment, the first hydrogel-forming composition comprises a plurality of nutrients to facilitate growth of aerobic bacteria and/or aerotolerant bacteria. Suitable nutrients to facilitate growth of aerobic bacteria and/or aerotolerant bacteria are known to a person having ordinary skill in the art. In any embodiment, the first hydrogel-forming composition may comprise one or more of such nutrients.

Culture media (e.g., dehydrated, powdered culture media) comprising nutrients to facilitate the growth and reproduction of aerobic and aerotolerant bacteria are known in the art. Components of the culture media include, for example, a source of nitrogen (e.g., yeast extract, enzymatic digests of meat or other proteins, malt extract); a source of carbon (e.g., various sugars, polysaccharides, oligosaccharides, other carbohydrates); one or more various inorganic salts (e.g., calcium chloride, ferric ammonium citrate, magnesium sulfate, manganese chloride, zinc sulfate); and, optionally, a buffering agent. In view of the present disclosure, a person having ordinary skill in the art will recognize a variety of nutrient compositions that can be used with the enzyme substrate indicator agents of the present disclosure to detect aerobic and aerotolerant bacteria, provided a component of the nutrient composition does not substantially inhibit the hydrolysis of the enzyme substrates and provided a component of the nutrient composition does not substantially mask (e.g., by fluorescence quenching) the products of the enzyme substrates used as indicator agents.

In any embodiment, the culture device can comprise a nutrient that includes proteins, oligopeptides, and/or amino acids. Non-limiting examples of such nutrients include yeast extract (e.g., yeast autolysate) and protein digest. Nonlimiting examples of suitable nutrients to facilitate growth of aerobic bacteria and/or aerotolerant bacteria are shown in Table 1. The first hydrogel-forming composition can be provided in the device 100 as powder (or agglomerated powder) coating or as a dried liquid coating. The processes for preparing such powder coatings and liquid coatings and for adhering the coatings to a substrate sheet are known in the art and can be found, for example, in U.S. Pat. Nos. 4,565,783; 5,601,998; 5,364,766; and 5,681,712; each of which is incorporated herein by reference in its entirety.

TABLE 1

List of exemplary nutrients to facilitate growth of aerobic bacteria and/or aerotolerant bacteria.

Glucose
Pyruvate
Succinate
Casein hydrolysate
Brain Heart Infusion
Meat Peptone
Protein hydrolysate
Tryptone
Yeast Autolysate
Yeast Extract
Phytone Peptone
Meat Extract
Tryptose It is now known that at least one of or a combination of any two or more of L-arginine, skim milk, and D-trehalose can facilitate growth and detection of certain aerobic or aerotolerant within about 22-26 hours of incubation. Thus, in any embodiment, a culture device of the present disclosure can optionally comprise L-arginine, skim milk, D-trehalose, or a combination of any two or more of the foregoing nutrients. In any embodiment, the L-arginine can be present in a dried coating (e.g., the first hydrogel-forming composition) in a culture device of the present disclosure at a concentration of about 0.2-0.6% (e.g., about 0.5%) of the dry solids. In any embodiment, the skim milk can be present in a dried coating (e.g., the first hydrogel-forming composition) in a culture device of the present disclosure at a concentration of about 0.5-3.0% (e.g., about 1.2%) of the dry solids. In any embodiment, the D-trehalose can be present in a dried coating (e.g., the first hydrogel-forming composition) in a culture device of the present disclosure at a concentration of about 0.5-2.0% (e.g., about 1.2%) of the dry solids. In any embodiment, the L-arginine, skim milk, and D-trehalose cumulatively can be present in a dried coating (e.g., the first hydrogel-forming composition) in a culture device of the present disclosure at a concentration of less than or equal to about 5% of the dry solids.

In any embodiment, the culture device can comprise a buffering agent. The buffering agent can be provided in the first and/or second hydrogel-forming composition. Nonlimiting examples of suitable buffering agents include proteins, phosphate compounds (e.g., sodium dihydrogen phosphate, disodium hydrogen phosphate, potassium dihydrogen phosphate, dipotassium hydrogen phosphate), sodium carbonate, MOPS (2[N-Morpholino]ethanesulfonic acid) free acid, and MOPS sodium salt.

The culture device of the present disclosure can comprise one or more inorganic elements to facilitate the growth of aerobic or aerotolerant bacteria. These include any one or more of the following (to the extent not already provided in the above sources of various components of nutrients): calcium, chloride, cobalt, iron, manganese, phosphorus, potassium, sulfur, sodium, tin, and zinc. Salts may be provided as a source of ions. Salts may include potassium phosphate, magnesium sulfate, sodium chloride, calcium chloride, boric acid, copper sulfate, potassium iodide, ferric chloride, manganese sulfate, sodium molybdate, and zinc sulfate. The inorganic element(s) and/or salt(s) can be provided in the first hydrogel-forming composition and/or second hydrogel-forming composition, if present.

Table 2 shows one embodiment of a nutrient mixture that facilitates growth of aerobic and aerotolerant bacteria. Other nutrient mixtures known in the art can be used in a culture device of the present disclosure to facilitate growth of an aerobic or aerotolerant bacterium.

TABLE 2

Nutrient mixture used to facilitate growth of aerobic or aerotolerant bacteria.

Meat peptone (porcine)
Soytone
Tryptone
Yeast Extract
Pyruvic Acid
Potassium Phosphate (monobasic)
Potassium Phosphate (dibasic)
Dextrose
Magnesium sulfate (heptahydrate)
Calcium Chloride
Manganese Chloride
Sodium Carbonate
Zinc Sulfate (heptahydrate)

Attached to the substrate sheet 10, either directly or indirectly, is a cover sheet 20. The cover sheet 20 has a first major surface 20a and a second major surface 20b opposite the first major surface. In any embodiment, a portion (e.g., along an edge) of the cover sheet 20 can be affixed directly to a portion (e.g., a portion along one edge) of the substrate sheet 10 (e.g., via heat sealing or a double-sided tape 56). Alternatively, or additionally, a portion of the cover sheet 20 can be attached to a layer (e.g., first layer 12 and/or second layer 14) that is adhered directly or indirectly to the substrate sheet 10.

The cover sheet 20 is dimensioned to cover the sample-receiving zone that is disposed between the substrate sheet 10 and the cover sheet 20. Thus, the cover sheet 20 preferably is approximately the same size and shape as the substrate sheet 10. In any embodiment, the cover sheet 20 may comprise a tab 27 that extends beyond an edge of the substrate sheet 10. In any embodiment, the tab 27 may be proximate an edge of the substrate sheet 10 opposite an edge to which the cover sheet 20 is coupled to the substrate sheet 10, as shown in FIG. 1. In use, the tab 27 can be grasped in order to lift a portion of the cover sheet 20 away from the substrate sheet 10 to deposit a sample in the sample-receiving zone 30.

Cover sheet 20 is translucent or preferably transparent to facilitate counting of the bacterial colonies, and is substantially impermeable to both microorganisms and water vapor. Generally, cover sheet 20 will have the same properties, such as transparency and preferred water impermeability, as substrate sheet 10. Furthermore, cover sheet 20 can have patterns imprinted thereon, such as square grid pattern, or a mask-edge (not shown) to aid in the counting of bacterial colonies, to provide a target for placement of the aqueous test sample, and/or for aesthetic reasons. Cover sheet 20 can be selected to provide an amount of oxygen transmission necessary for aerobic bacteria, some of which may prefer relatively oxygen-rich environments for optimal growth conditions. Suitable cover sheet materials are disclosed in U.S. Pat. No. 5,681,712.

In any embodiment, the cover sheet 20 can be free of any coating, or a portion of the cover sheet can be coated (e.g., on the major surface facing the substrate sheet 10) with a third layer 22 of a second adhesive composition, in order to facilitate sealing of the cover sheet 20 over the first layer 12. Furthermore, a portion of the cover sheet 20 or the third layer 22 can optionally be coated (e.g., on the major surface facing the substrate sheet 10) with a fourth layer 24 comprising a second hydrogel-forming composition.

In any embodiment, the second adhesive composition of the third layer 22 can be the same as or different from first adhesive composition. In any embodiment, the second hydrogel-forming composition can comprise the same components or different components as the first hydrogel-forming composition. Coatings on cover sheet 20 can cover the entire surface facing the substrate sheet 10, but preferably cover at least the part of the surface that is in fluid communication with the sample-receiving zone 30. Such coated cover sheets are particularly preferred when it is desired to provide a device with more gelling agent than can be incorporated in the first hydrogel-forming composition alone. At least a portion of the third layer 22, if present, and the fourth layer, if present, is in fluidic communication with the sample-receiving zone 30 after the device 100 is hydrated with a predetermined quantity of an aqueous liquid.

Figure 3:
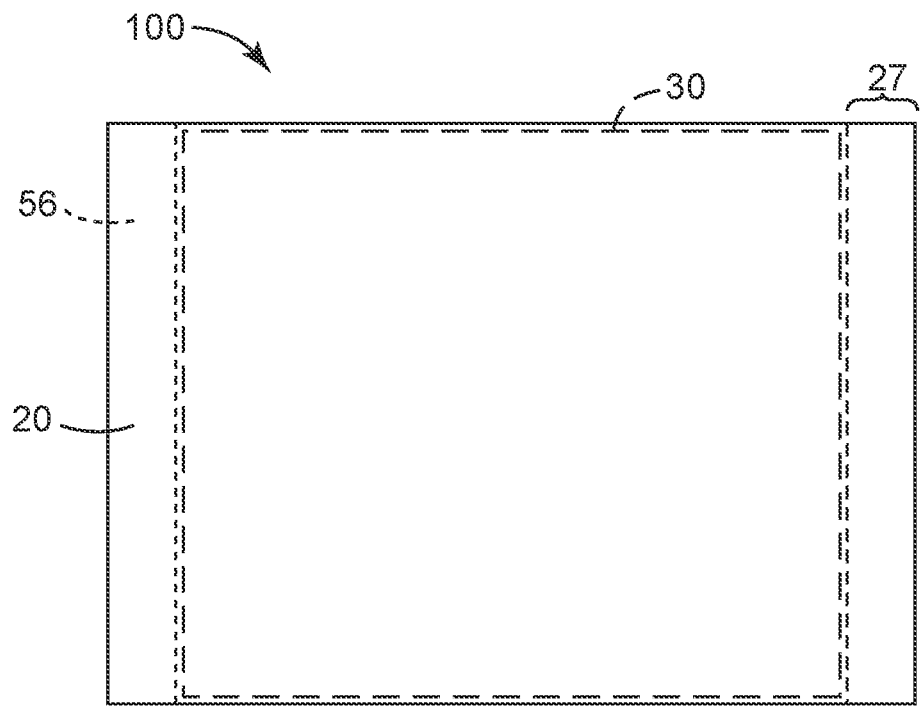
FIG. 3 is a plan view of the culture device of FIG. 1.

FIG. 3 shows a top view of the culture device 100 and highlighting the sample-receiving zone 30. A sample can be deposited into the culture device 100 in any part of the sample-receiving zone 30 although, preferably, the sample is deposited proximate the central region of the sample-receiving zone.

The fourth layer 24 comprises a substantially water-free, cold-water-soluble second hydrogel-forming composition. In any embodiment, the second hydrogel-forming composition of the fourth layer 24 comprises one or more cold water-soluble gelling agents (e.g., guar gum), as disclosed herein. In any embodiment, the second hydrogel-forming composition further can comprise an effective amount of one or more nutrient (e.g., tryptone) disclosed herein to facilitate growth of an aerobic or aerotolerant bacterium. In any embodiment, the second hydrogel-forming composition can comprise one or more indicator agent (e.g., 3-Indoxyl-phosphate) as disclosed herein. In any embodiment, the second hydrogel-forming composition comprises at least one cold water-soluble gelling agent, and one or more indicator agent or one or more nutrient. In any embodiment, the second hydrogel-forming composition can be applied to the third layer 22 comprising the second adhesive composition as a powder or agglomerated powder as described in U.S. Pat. No. 4,565,783, for example.

In any embodiment, the second hydrogel-forming composition of the fourth layer 24 can be applied to the third layer 22 as a substantially dry, powder (or agglomerated powder) coating. Suitable processes for preparing and applying such powder coatings is described in U.S. Pat. No. 4,565,783.

In use, an aqueous liquid (e.g., a sample material and/or a sample-suspending medium such as water, a buffer, or a nutrient medium) is deposited into the sample-receiving zone 30 of the culture device 100. When the aqueous liquid contacts a gelling agent (e.g. a gelling agent in the first hydrogel-forming composition and a gelling agent in the second hydrogel-forming composition, if present) the liquid combines with the gelling agent to form a hydrogel in the sample-receiving zone. The resulting hydrogel provides an aqueous environment to facilitate growth and detection of a colony of aerobic and/or aerotolerant bacteria.

The first adhesive composition and, if present, second adhesive composition preferably is a pressure sensitive adhesive. More preferably, the adhesive is a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer comprises a lower alkyl (C2 to C10) monomer of acrylic acid, including, for example, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl (C2 to C5))(meth)acrylamides, N-methyl(meth)acrylamide, N,N-dimethyl(meth) acrylamides, or mixtures thereof.

In any embodiment, the first adhesive composition and/or second adhesive composition may comprise an indicator agent. In any embodiment, the indicator agent may be dissolved in an organic solvent (e.g., methanol) and blended with the adhesive composition before applying the composition to the substrate sheet 10 and/or cover sheet 20. In any embodiment, the first adhesive composition and/or second adhesive composition may include a plurality of indicator agents, as discussed herein. In any embodiment the first adhesive composition and second adhesive composition each may include an identical indicator agent. In any embodiment the first adhesive composition and second adhesive composition each may include an indicator agent that is not included in the other adhesive composition.

In any embodiment, first hydrogel-forming composition and/or second hydrogel-forming composition may comprise an indicator agent. In any embodiment, first hydrogel-forming composition comprises at least one indicator agent and the second hydrogel-forming composition may comprises at least one indicator agent.

A culture device 100 of the present disclosure comprises a plurality of indicator agents for detecting a presence of an aerobic or aerotolerant bacterium. In any embodiment, suitable indicator agents comprise, for example, enzyme substrates. In any embodiment, each indicator agent can comprise a reporter group (e.g., a fluorogenic group or chromogenic group) that permits detection of a reaction between the indicator agent and a biological activity (i.e., an enzyme activity associated with an aerobic or aerotolerant bacterium) and the indicator agent. In any embodiment, the plurality of indicator agents can comprise five indicator agents. In any embodiment, the five indicator agents can include three agents for detecting three distinct glycosidase enzyme activities, an indicator agent for detecting an esterase enzyme activity (e.g., an alkyl esterase enzyme activity), and an indicator agent for detecting a phosphatase enzyme activity.

Species of aerobic and/or aerotolerant bacteria may produce one or more of a variety of glycosidase enzyme activities, each glycosidase enzyme activity being capable of reacting with an indicator reagent to produce a detectable product. Tables 3 and 4 list nonlimiting examples of indicator agents that may react with a corresponding enzyme activity, if present, within or proximate a colony of aerobic or aerotolerant bacteria.

TABLE 3

| Indicator agents for detecting glycosidase enzyme activities. | | |
|---|---|---|
| 4-Methylumbelliferyl-N-acetate-β-D-galactosaminide | 4-Methylumbelliferyl-β-D-xylose | 4-Nitrophenyl-β-D-fucopyranoside |
| 4-Methylumbelliferyl-N-acetate-β-D-glucosaminide | 6-Bromo-2-naphthyl-N-acetyl-β-D-glucosaminide | 2-Nitrophenyl-β-D-thiogalactopyranoside |
| 2'-(4-Methylumbelliferyl-α-D-N-acetyl-neuraminic acid Sodium salt | 6-Bromo-2-naphthyl-α-D-glucopyranoside | Phenolphthalein-mono-β-D-galactopyranoside |
| 4-Methylumbelliferyl-α-L-arabinapyranoside | 6-Bromo-2-naphthyl-β-D-xylopyranoside | 5-Bromo-4-chloro-3-Indolyl-N-acetyl-β-D-galactosaminide |
| 4-Methylumbelliferyl-β-D-cellobiopyranoside | Naphthol AS-BI-β-L-fucopyranoside | 5-Bromo-4-chloro-3-Indolyl-β-D-fucopyranoside |
| 4-Methylumbelliferyl-β-D-fucoside | 1-Naphthyl-α-D-glactopyranoside | Indoxyl-β-D-galactoside |
| 4-Methylumbelliferyl-α-D-mannoside | 2-Nitrophenyl-N-acetyl-α-D-galactosaminide | 4-Nitrophenyl-α-L-fucopyranoside |
| 4-Methylumbelliferyl-6-sulfo-N-acetyl-β-D-glucosaminide | 4-Nitrophenyl-β-D-cellobioside | 4-Nitrophenyl-β-L-fucopyranoside |
| 4-Methylumbelliferyl-β-D-cellotriose | 6-Bromo-2-naphthyl-β-D-galactoside | 2-Nitrophenyl-α-D-galactopyranoside |
| 4-Methylumbelliferyl-β-D-N,N'-diacetyl-chitobioside | 6-Bromo-2-naphthyl-β-D-glucopyranoside | 2-Nitrophenyl-β-D-galactopyranoside |
| 4-Methylumbelliferyl-α-L-fucoside | 6-Bromo-2-naphthyl-β-D-glucouronide | 3-Nitrophenyl-α-D-galactopyranoside |
| 4-Methylumbelliferyl-β-L-fucoside | 2-Chloro-4-nitrophenyl-N-acetyl-β-D-glucosaminide | 3-Nitrophenyl-β-D-galactopyranoside |
| 4-Methylumbelliferyl-α-D-galactoside | 2-Chloro-4-nitrophenyl-β-D-cellobioside | 4-Nitrophenyl-α-D-galactopyranoside |
| 4-Methylumbelliferyl-β-D-galactoside | 2-Chloro-4-nitrophenyl-β-D-xylopryanoside | 4-Nitrophenyl-β-D-galactopyranoside |
| 4-Methylumbelliferyl-β-D-galactoside-6-phosphate Ammonium salt | β-Hydroxyquinoline-β-D-glucuronide | 4-Nitropheny l-β-D-galacturonide |
| 4-Methylumbelliferyl-α-D-gluoside | Naphthol AS--BI-β-D-galactopyranoside | 4-Nitrophenyl-α-D-glucopyranoside |
| 4-Methylumbelliferyl-β-D-gluoside | Naphthol AS--BI-β-D-galaclosaminide | 4-Nitrophenyl-β-D-glucopyranoside |
| 4-Methylumbelliferyl-β-D-glucuronide | Naphthol AS--BI-glucopyranoside | 4-Nitrophenyl-β-D-glucuronide |
| 4-Methylumbelliferyl-β-D-N,N',N'-triacetylchitotriose | Naphthol AS--BI-β-D-glucuronic acid | 2-Nitrophenyl-β-D-glucuronide |
| 5-Bromo-4-chloro-3-Indolyl-α-D-galactopyranoside | 1-Naphthyl-β-D-glactopyranoside | 4-Nitrophenyl-β-D-glucuronide |
| 4-Nitrophenyl-N-acetyl-1-thio-β-D-glucosaminide | 2-Naphthyl-β-D-galactopyranoside | 4-Nitrophenyl-β-D-thiogalactopyranoside |
| 4-Nitrophenyl-α-L-arabinopyranoside | 1-Naphthyl-β-D-glucuronide | 4-Nitrophenyl-β-D-thioglucopyranoside |
| 3-Nitrophenyl-β-D-fucopyranoside | 4-Nitropheny l-N-acetyl-α-D-galactosaminide | Phenolphthalein-β-D-glucuronic acid Sodium salt |
| 4-Nitrophenyl-α-D-fucopyranoside | 4-Nitropheny l-N-acetyl-β-D-galactosaminide | Phenyl-N-acetyl-α-D-glucosaminide |
| 5-Bromo-4-chloro-3-Indolyl-β-D-glucopyranoside | 4-Nitrophenyl-N-acetyl-α-D-glucosaminide | Phenylethyl-β-D-galactoside |
| 5-Bromo-4-chloro-3-Indolyl-β-D-glucuronic acid Cyclohexylammonium salt | 4-Nitrophenyl-N-acetyl-β-D-glucosaminide | Phenyl-β-D-galactoside |
| 5-Bromo-4-chloro-3-Indolyl-β-D-glucuronic acid Sodium salt | Indoxyl-β-D-glucoside | Phenyl-α-D-glucoside |
| 5-Bromo-4-chloro-3-Indolyl-α-D-mannopyranoside | Indoxyl-β-D-glucuronic acid Cyclohexylammonium salt | 5-Bromo-4-chloro-3-Indolyl-N-acetyl-β-D-glucosaminide |
| 5-Bromo-4-chloro-3-Indolyl-β-D-galactopyranoside | 5-Bromo-4-chloro-3-Indolyl-α-D-glucopyranoside | |

TABLE 3-continued

Indicator agents for detecting glycosidase enzyme activities.

| | | |
|---|---|---|
| ALDOL 467 β-D-glucosaminide | ALDOL 470 α-D-glucopyranoside | ALDOL 470 β-D-galactopyranoside |
| ALDOL 518 β-D-galactopyranoside | ALDOL 467 β-D-galactopyranoside | ALDOL 458 β-D-galactopyranoside |

Species of aerobic or aerotolerant bacteria may produce a variety of esterase enzyme activities including, for example, alkyl esterase (e.g., fatty acid alkyl esterase) enzyme activities and phosphatase (e.g., phosphoric monoester hydrolase) enzyme activities. Table 4 lists nonlimiting examples of indicator agents that may react with a corresponding esterase enzyme activity, if present, within or proximate a colony of aerobic or aerotolerant bacteria.

TABLE 4

Indicator agents for detecting alkyl esterase and phosphatase enzyme activities.

| Alkyl esterase enzyme substrates | Phosphatase enzyme substrates |
|---|---|
| 4-Methylumbelliferyl-acetate | Bis(4-methylumbelliferyl)-phosphate |
| 4-Methylumbelliferyl-butyrate | Bis(4-methylumbelliferyl)-phosphate Sodium salt |
| 4-Methylumbelliferyl-laurate | 4-Methylumbelliferyl-phosphate (free acid) |
| 4-Methylumbelliferyl-nonaoate | 4-Methylumbelliferyl-phosphate Dicyclohexylammonium salt |
| 4-Methylumbelliferyl-oleate | 4-Methylumbelliferyl-phophate Disodium salt |
| 4-Methylumbelliferyl-palmitate | Bis(4-nitrophenyl)phosphate Sodium salt |
| 4-Methylumbelliferyl-propionate | Naphthol AS-phosphate |
| 4-Methylumbelliferyl-stearate | Naphthol AS-phosphate Sodium salt |
| 6-Bromo-2-naphthyl acetate | 1-Naphthylphosphate Disodium salt |
| Naphthol AS-acetate | 2-Naphthylphosphate Disodium salt |
| Naphthol AS-nananoate | 2-Naphthylphosphate Sodium salt |
| 1-Naphthylbutyrate | 2-Naphthylphosphate Sodium salt |
| 2-Naphthylbutyrate | 1-Naphthylphosphate Sodium salt |
| 1-Naphthylcaprylate | Phenolphthalein diphosphate |
| 2-Naphthylcaprylate | Phenolphthalein diphosphate Tetrasodium salt |
| 2-Nitrophenyl-acetate | 5-Bromo-4-chloro-3-Indolyl-phosphate Disodium salt |
| 4-Nitrophenyl-acetate | 5-Bromo-4-chloro-3-Indolyl-phosphate Potassium salt |
| 2-Nitrophenyl-butyrate | 5-Bromo-4-chloro-3-Indolyl-phosphate p-Toluidine salt |
| 4-Nitrophenyl-butyrate | 3-Indoxyl-phosphate Di(2-amino-2-methyl-1,3-propanediol) salt |
| 4-Nitrophenyl-caprate | 3-Indoxyl-phosphate Disodium salt |
| 4-Nitrophenyl-caproate | 3-Indoxyl-phosphate p-Toluidine salt |
| 3-Nitrophenyl-capry late | ALDOL 470 phosphate, disodium salt |
| 4-Nitrophenyl-caprylate | ALDOL 458 phosphate, disodium salt |
| 2-Nitrophenyl-myristate | |
| 4-Nitrophenyl-myristate | |
| 2-Nitrophenyl-palmitate | |
| 4-Nitrophenyl-palmitate | |
| 4-Nitrophenyl-propionate | |
| 4-Nitrophenyl-stearate | |
| 5-Bromo-4-chloro-3-Indolyl-acetate | |
| 5-Bromo-4-chloro-3-Indolyl-butyrate | |
| 5-Bromo-4-chloro-3-Indolyl-caprylate | |
| ALDOL 515 acetate | |
| ALDOL 470 acetate | |
| ALDOL 470 butyrate | |
| ALDOL 470 nanoate | |
| ALDOL 458 acetate | |

In a preferred embodiment, the culture device of the present disclosure comprises an indicator agent for detecting α-glucosidase enzyme activity, an indicator agent for detecting β-glucosidase enzyme activity, and an indicator agent for detecting β-galactosidase enzyme activity. In any embodiment, all three of the aforementioned indicator agents comprise similar or identical reporter groups. In a particularly preferred embodiment, the culture device of the present disclosure comprises 5-bromo-4-chloro-3-indolyl-α-D-glucopyranoside, 5-bromo-4-chloro-3-indolyl-β-D-glucopyranoside, and 5-bromo-4-chloro-3-indolyl-β-D-galactopyranoside. In an embodiment, the culture device of the present disclosure further comprises a redox indicator agent. A non-limiting example of a suitable redox indicator agent is triphenyltetrazolium chloride. In any embodiment, the redox indicator agent can be disposed in the first adhesive composition and/or the second adhesive composition. In any embodiment, a plurality of enzyme substrate indicator agents can be disposed in one adhesive composition (e.g., the first adhesive composition) and a redox indicator agent can be disposed in another adhesive composition (e.g., the second adhesive composition).

Suitable redox indicators (e.g., triphenyltetrazolium chloride) include a reporter group (e.g., a chromogenic and/or fluorogenic group) that is oxidized or reduced to form a detectable signal (e.g. a detectable color change or fluorescence change). For example, triphenyl tetrazolium chloride is reduced by bacteria to form a formazan product having a detectable color. Detecting the detectable reporter group (e.g., formazan) in a culture device of the present disclosure is indicative of a possible presence of an aerobic or aerotolerant bacterium.

According to the present disclosure, the plurality of indicator agents can be provided in the culture device 100 in one or more of the layers disposed on the substrate sheet 10 or the cover sheet 20. In any embodiment, one or more indicator agent can be provided in the first layer 12. In these embodiments, at least one indicator agent can be mixed with the cold water-soluble gelling agent and optional nutrient of the first hydrogel-forming composition and coated onto at least a portion of the substrate sheet 10 (and/or a portion of the second layer, if present) therewith.

In any embodiment, one or more indicator agent can be provided in the second layer 14. In these embodiments, at least one indicator agent can be mixed with the adhesive of the first adhesive composition and coated onto at least a portion of the substrate sheet 10 therewith.

In any embodiment, one or more indicator agent can be provided in the third layer 22. In these embodiments, at least one indicator agent can be mixed with the adhesive and optional selective agent of the second adhesive composition and coated onto at least a portion of the cover sheet 20 therewith.

In any embodiment, one or more indicator agent can be provided in the fourth layer 24. In these embodiments, at least one indicator agent can be mixed with the cold water-soluble gelling agent and optional nutrient of the second hydrogel-forming composition and coated onto at least a portion of the cover sheet 20 (and/or a portion of the third layer 22, if present) therewith.

Advantageously, when provided in at least one of the adhesive compositions, the one or more indicator agent can be uniformly distributed within the sample-receiving zone 30 of the culture device and can be provided in the adhesive composition at a very high concentration. Without being bound by theory, it is thought the indicator agents efficiently partition from the relatively hydrophobic adhesive composition into the relatively hydrophilic reconstituted gel, thereby providing consistent, uniform concentrations of the indicator agents to react with aerobic or aerotolerant bacteria, if present in the sample, in the culture device.

In any embodiment, the first and/or second adhesive composition can comprise a plurality of indicator agents (e.g., at least five indicator agents) or salts thereof. The plurality of indicator agents (or salts thereof) can comprise 5-Bromo-4-chloro-3-indolyl acetate, 5-Bromo-4-chloro-3-indolyl-β-D-galactopyranoside, 5-Bromo-4-chloro-3-indolyl-β-D-glucopyranoside, 5-Bromo-4-chloro-3-indolyl-α-D-glucopyranoside, 5-Bromo-4-chloro-3-indolyl phosphate p-toluidine salt and TTC. The investigators have found this particular combination of indicator agents has the surprising effect of providing for the detection of at least one organism (e.g., a microorganism belonging to the genus *Pseudomonas* and the lactic acid bacteria group) that cannot otherwise be detected using a similar culture device having only chromogenic enzyme substrates or redox substrates, indicating a possible synergistic effect of the combination.

In any embodiment, the first and/or second adhesive composition cumulatively can comprise about 0.05-1.0 weight percent 5-Bromo-4-chloro-3-indolyl acetate, about 0.05-1.0 weight percent 5-Bromo-4-chloro-3-indolyl-β-D-galactopyranoside, 0.05-1.0 weight percent 5-Bromo-4-chloro-3-indolyl-β-D-glucopyranoside, about 0.05-1.0 weight percent 5-Bromo-4-chloro-3-indolyl-α-D-glucopyranoside and/or about 0.05-1.0 weight percent 5-Bromo-4-chloro-3-indolyl phosphate p-toluidine salt.

In any embodiment, the first and/or second adhesive composition cumulatively can comprise about 0.18-0.5 weight percent 5-Bromo-4-chloro-3-indolyl acetate. In any embodiment, the first and/or second adhesive composition cumulatively can comprise about 0.34-0.72 weight percent 5-Bromo-4-chloro-3-indolyl-β-D-galactopyranoside. In any embodiment, the first and/or second adhesive composition cumulatively can comprise about 0.34-0.72 weight percent 5-Bromo-4-chloro-3-indolyl-β-D-glucopyranoside. In any embodiment, the first and/or second adhesive composition cumulatively can comprise about 0.34-0.72 weight percent 5-Bromo-4-chloro-3-indolyl-α-D-glucopyranoside. In any embodiment, the first and/or second adhesive composition cumulatively can comprise about 0.36-0.76 weight percent 5-Bromo-4-chloro-3-indolyl phosphate p-toluidine salt.

In any embodiment, the first and/or second adhesive composition cumulatively can comprise about 0.18-0.5 weight percent 5-Bromo-4-chloro-3-indolyl acetate, about 0.34-0.72 weight percent 5-Bromo-4-chloro-3-indolyl-β-D-galactopyranoside, about 0.34-0.72 weight percent 5-Bromo-4-chloro-3-indolyl-β-D-glucopyranoside, about 0.34-0.72 weight percent 5-Bromo-4-chloro-3-indolyl-α-D-glucopyranoside, and about 0.36-0.76 weight percent 5-Bromo-4-chloro-3-indolyl phosphate p-toluidine salt.

In any embodiment, the first and/or second hydrogel-forming composition can contain gelling agent only, and no nutrient or indicator agent. In any embodiment, one or more nutrient to facilitate growth of an aerobic or aerotolerant bacterium can be deposited into the culture device (e.g., in the sample-receiving zone 30) in an aqueous liquid (e.g., an aqueous suspending medium or diluent) when the culture device is inoculated.

As discussed above, the first and/or second hydrogel-forming composition of any culture device of the present disclosure further may comprise at least one nutrient to facilitate the growth of an aerobic or aerotolerant bacterium. Species of aerobic and aerotolerant bacteria are metabolically and ecologically diverse and, thus, can utilize a variety of nutrients to support their growth and reproduction. Table 5 shows nonlimiting examples of genera that include aerobic and aerotolerant bacteria according to the present disclosure.

TABLE 5

Exemplary genera of aerobic and aerotolerant bacteria.

*Alkaligenes*
*Bacillus*
*Citrobacter*
*Enterobacter*
*Enterococcus*
*Escherichia*
*Haemophilus*
*Kokuria*
*Microbacterium*
*Proteus*
*Pseudomonas*
*Staphylococcus*
*Streptococcus*
*Vibrio*
*Yersinia*

Figure 4:
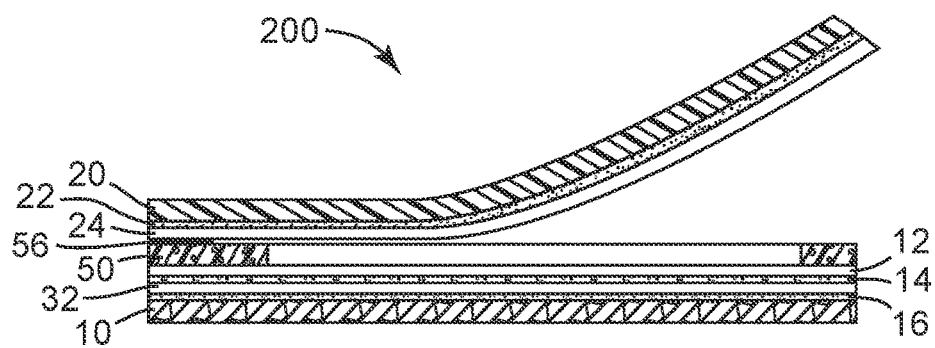
FIG. 4 is a schematic cross-sectional side view of an alternative embodiment of a culture device of the present disclosure.
Figure 5:
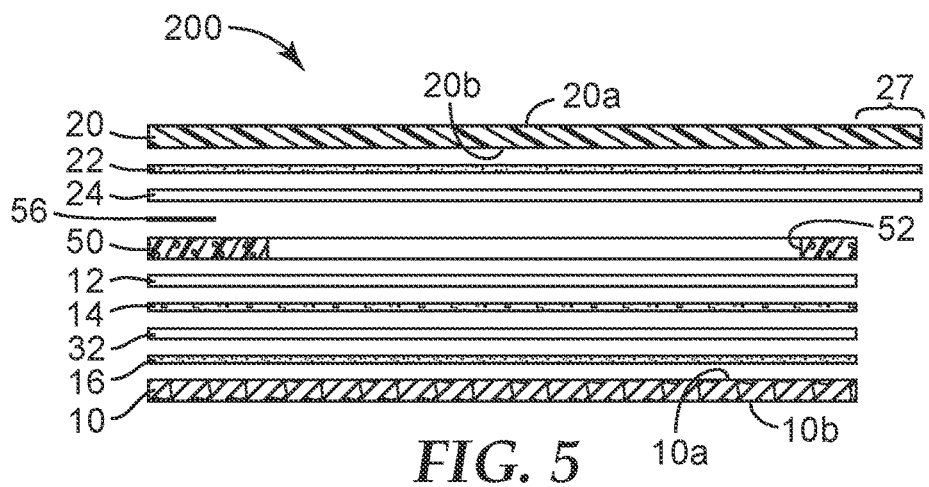
FIG. 5 is an exploded schematic cross-sectional side view of the culture device of FIG. 4.
Figure 6:
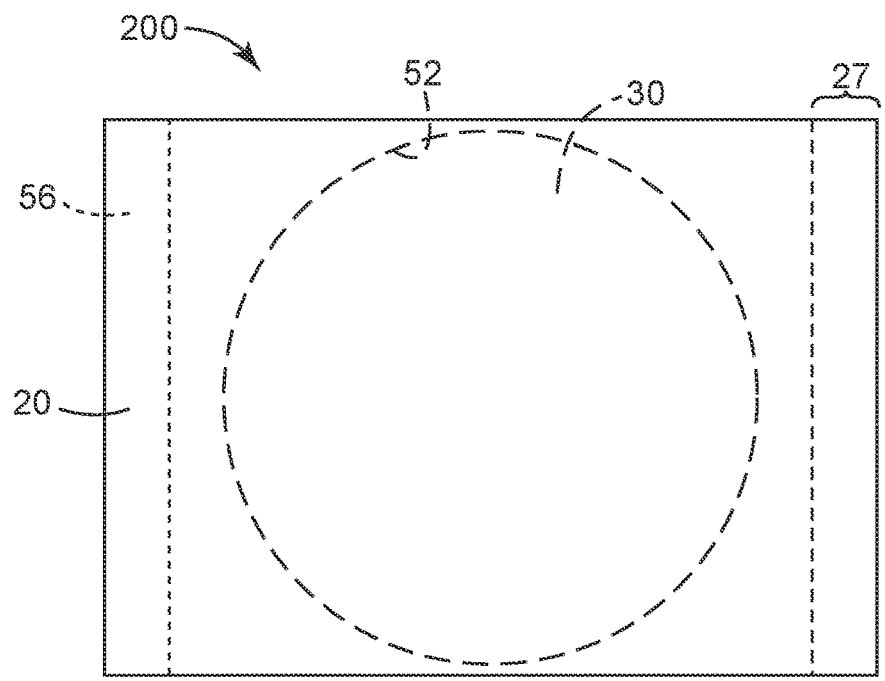
FIG. 6 is a plan view of the culture device of FIG. 4.

In any embodiment, a culture device of the present disclosure further comprises an air-permeable membrane that facilitates aerobic growth of an aerobic or aerotolerant bacterium disposed in the culture device. FIGS. 4-6 show one embodiment of a culture device 200 comprising an air-permeable membrane 32.

The culture device 200 comprises a substrate sheet 10, first layer 12 comprising a first hydrogel-forming composition, and cover sheet 20; each as described hereinabove. The cover sheet 20 is attached, either directly or indirectly, to the substrate sheet 10 as described hereinabove. In any embodiment, the culture device 200 further comprises optional second layer 14 that comprises a first adhesive composition, and/or optional third layer 22 that comprises a second adhesive composition, and/or optional fourth layer 24 that comprises a second hydrogel-forming composition; each as described hereinabove.

In any embodiment, the air permeable membrane 32 may be adhered to the substrate sheet 10 (e.g., via adhesive layer 16). Adhesive layer 16 may comprise a third adhesive composition. The third adhesive composition can comprise the same adhesive components as the first or second adhesive compositions described herein and may be applied to the substrate sheet 10 via a knife coating process, for example. The method of fixing the microporous membrane 32 to substrate sheet 10 will depend on the nature of adhesive composition in the second layer 14. If the adhesive composition is pressure sensitive for instance, the microporous membrane 32 can be placed on the second layer 14, pressed down, and thereby adhered in place. In any embodiment, the microporous membrane 32 can be translucent or substantially transparent when wet in order to enable viewing microbial colonies.

In the illustrated embodiment of FIGS. 4-6, the air-permeable membrane 32 is adhered to the substrate sheet 10 via adhesive layer 16. Disposed on (e.g., coated onto) at least a part (or all) of the air permeable membrane 32 is the optional second layer 14. The second layer 14 comprises a first adhesive composition as described herein. The first adhesive composition may comprise one or more indicator agents as described herein. Disposed on (e.g., coated onto) at least a part (or all) of the second layer 14 is the first layer 12. The first layer 12 comprises the first hydrogel-forming composition as described herein.

Without being bound by theory, the air-permeable membrane 32 allows an adequate supply of air to the first layer 12 comprising the hydrogel-forming composition when the cover sheet 20 is in place after the device is inoculated. In so doing, the membrane 32 is useful for supporting growth of aerobic microorganisms in the device. By virtue of the air permeability of the membrane 32 and the membrane being substantially exposed at its edge(s) to air, air is able to pass into the edge(s) of the membrane, horizontally through the membrane, and into the first layer 12. Horizontal passage of air for a particular membrane is most conveniently estimated by evaluating the vertical air permeability of the membrane (i.e., permeability in a direction normal to the top and bottom surfaces of the membrane). Suitable air permeable membrane 32 materials, including microporous films and microporous non-woven webs of synthetic or natural materials, are described in U.S. Pat. No. 5,089,413, which is incorporated herein by reference in its entirety. A nonlimiting example of a preferred membrane material is a microporous polyolefin film (APTRA Classic; RKW Danafilms; Westborough, Mass.).

In any embodiment, the air-permeable membrane 32 is substantially opaque. In these embodiments, if the substrate sheet 10 comprises grid lines disposed (e.g., printed) thereon, preferably the grid lines are substantially not visible when the culture device 100 is illuminated by a light source facing the first major surface 20a of the cover sheet 20 (i.e., "front-side" illumination). However, it is preferred that grid lines (not shown) disposed on the substrate 10 are substantially visible when the culture device 100 is illuminated by a light source facing the second major surface 10b of the substrate sheet (i.e., "back-side" illumination). Advantageously, this configuration of the air-permeable membrane 32 provides brilliant colony colors and ease for counting colonies visually by a human operator under ambient lighting (i.e., the grid does not blend with or obscure any colonies when the device is "top-lit"), while also providing a grid to facilitate counting, if desired, when the device is "back-lit".

The air-permeable membrane 32 may be any of a variety of colors, provided the color does not substantially interfere with detection of the typical colony colors (i.e., blue, red, violet). Light-colored membranes are preferred. In any embodiment, the air-permeable membrane is white. In any embodiment, the air-permeable membrane is white when it is in fluid contact with the aqueous sample deposited into the growth zone.

In any embodiment, the substrate sheet 10 or the membrane 32 has a visible square grid pattern printed upon it, as described in U.S. Pat. No. 4,565,783; to facilitate the counting of bacterial colonies. A device of the present disclosure can be prepared using a variety of techniques. Generally, a device can be made by hand or with common laboratory equipment as described in U.S. Pat. No. 4,565,783.

In any embodiment of the present disclosure, adhered to the substrate sheet 10, either directly or indirectly, is a spacer 50. As depicted in FIGS. 4-6, the culture device 200 includes a spacer 50 attached (e.g., via heat bonding or a pressure-sensitive adhesive) to the first surface 10a of substrate sheet 10, the first layer 12, and or the second layer 14. The spacer 50 comprises an aperture (e.g., circular aperture 52) cut through the center to expose the first layer 12. The walls of aperture 52 provide a well of predetermined size and shape that defines the sample-receiving zone 30 of the culture device 200. The spacer 50 confines the hydrogel following hydration of the first hydrogel-forming composition in the sample-receiving zone with an aqueous liquid. The aperture 52 generally delineates a growth area of the culture device. Spacer 52 should be thick enough to form a well of the desired volume, e.g., 1, 2 or 3 milliliters. Closed cell polyethylene or polystyrene foams, for example, are preferred materials for spacer 50, but any material which is hydrophobic (non-wetting), inert to microorganisms, and capable of withstanding sterilization may be used. In some embodiments (not shown), the spacer can comprise a plurality of apertures (e.g., 2, 3, 4, 5, 6, 7, 8, 9, 10, 12, 15, or 20 apertures), each of which can be inoculated with a distinct sample.

Suitable materials for the spacer member are any solid non-inhibitory natural or synthetic substance which is readily available in sheet form but is not a microorganism growth site. Polyethylene, polypropylene, polyethylene terephthalate and polystyrene are a few examples of suitable synthetic materials. In particular, relatively inexpensive commercially available polystyrene foams and polyethylene foams are preferred.

Spacer 50 can include relatively thick designs, such as those described in U.S. Pat. No. 5,681,712. One purpose of the thicker (e.g., at least about 0.5 mm thick, about 1 mm thick, about 1.5 mm thick and about 2 mm thick) apertured spacer 50 is to locate and protect membranes (e.g. membrane filters, not shown) that are placed in the aperture 52 of the spacer 50 in contact with the first hydrogel-forming composition. In any embodiment, another purpose of the thicker spacer 50 is to reduce or prevent contact by cover sheet 20 with the growing colonies of microorganisms (i.e., provide a "head space" between the growth surface and the cover sheet 20, which can also provide increased aeration for growing colonies of aerobic or aerotolerant microorganisms).

In any embodiment of a culture device comprising a spacer 50, the cover sheet 20 is preferably adhered in a hinge-like fashion along one edge of spacer 50. Optionally, the cover sheet 20 is coated with a third layer 22 comprising a second adhesive composition and a fourth layer 24 comprising a second hydrogel-forming composition, each as described herein. In any embodiment, the second adhesive composition can comprise one or more (e.g., all) of the plurality of indicator agents used to aerobic and/or aerotolerant bacteria.

In another aspect, the present disclosure provides a method of detecting an aerobic or aerotolerant bacterium. The method comprises contacting a sample and an aqueous liquid in the sample-receiving zone of any embodiment of the culture device of the present disclosure to form an inoculated culture device. In any embodiment, the sample can comprise the aqueous liquid. In general, the amounts of gelling agent; indicator agents; and nutrient (if present) in sample-receiving zone of the culture device are selected to provide an effective concentration for detecting aerobic or aerotolerant bacteria when they (i.e., the gelling agent, indicator agents, and nutrient) are reconstituted with a predetermined volume (e.g., 1 milliliter, 2 milliliters, 5 milliliters) of aqueous liquid. In any embodiment, the aqueous liquid can be added with the sample materials (e.g., the sample material can be dissolved, homogenized, suspended, and/or diluted in an aqueous liquid such as sterile water, an aqueous buffer, or an aqueous nutrient medium, for example). In any embodiment wherein the sample comprises solid (e.g., a membrane filter having retained material thereon or therein) or semisolid materials, the predetermined volume of liquid (e.g., sterile water, an aqueous nutrient medium) can be used to reconstitute the culture device before or after the solid or semisolid sample is used to inoculate the device.

In any embodiment of the method, a nutrient can be added (e.g., in an aqueous solution) to the device before, during, or after the addition of the sample to the device. In any embodiment, the nutrient can be added, for example, as a concentrated solution which, when mixed with the sample and/or diluent to achieve the predetermined volume, is diluted to the proper concentration in the inoculated culture device. In any embodiment, the nutrient added to the culture device can optionally comprise L-arginine, skim milk, D-trehalose, or a combination of any two or more of the foregoing nutrients.

The sample can be contacted with the sample-receiving zone of the culture device using methods that are known in the art (e.g., by pouring or pipetting a liquid sample into the culture device). In any embodiment, the coversheet is typically lifted to permit deposition of the sample between the coversheet and the substrate sheet; preferably, into the aperture of a spacer, if present, in the culture device. In any embodiment, contacting a sample and an aqueous liquid with the gelling agent in the sample-receiving zone forms an inoculated culture device. After forming the inoculated culture device, the cover sheet is lowered to form a protective barrier against contamination and/or excess evaporation of the aqueous liquid during incubation. In any embodiment, the sample may be spread evenly over the growth region, for example by placing a weighted plate on top of the covered device.

When using an embodiment of the culture device that does not comprise a spacer with an aperture as described above, a template (e.g., a weighted circular ring defining a growth region) can be applied temporarily on top of cover sheet 20, after closing, to confine reconstitution of the medium to a growth region defined by the template (e.g., a 5 cm-diameter circular growth region proximate the central region of the sample-receiving zone).

In any embodiment, contacting a sample with the first hydrogel-forming composition or second hydrogel-forming composition of the culture device comprises placing the sample in fluid communication with the at least one nutrient. This can be achieved by suspending or diluting the sample in a liquid (e.g., an aqueous liquid) comprising a nutrient or by contacting the sample and an aqueous liquid with a first hydrogel-forming composition or second hydrogel-forming composition, described herein, comprising the at least one nutrient. Thus, in any embodiment, contacting a sample material with the first hydrogel-forming composition or second hydrogel-forming composition of the culture device comprises placing the sample in fluid communication with a nutrient to facilitate growth of an aerobic or aerotolerant bacterium.

In any embodiment, the method further comprises incubating (e.g., in a temperature-controlled environmental chamber) the inoculated culture device for a period of time. The incubation conditions (e.g., the incubation temperature) can affect the rate of growth of aerobic and/or aerotolerant bacteria present in the sample. A person having ordinary skill in the art will recognize suitable incubation temperatures to detect specific aerobic and/or aerotolerant bacteria. An inoculated culture device of the present disclosure can be incubated, for example at temperatures between about 25° C. to about 42° C., inclusive, for example. In any embodiment, the culture device can be incubated in an aerobic (e.g., normal atmospheric) gaseous environment.

The inoculated culture device is incubated for a period of time sufficient to permit the growth of aerobic and/or aerotolerant bacteria. In any embodiment, the period of time can be about 22 hours to about 72 hours, inclusive. In any embodiment, the period of time can be about 22 hours to about 48 hours, inclusive. In any embodiment, the period of time can be about 22 hours to about 36 hours, inclusive. In any embodiment, the period of time can be about 22 hours to about 26 hours, inclusive. In any embodiment, the period of time can be about 24 hours. In any embodiment, the period of time can be up to about 48 hours. In any embodiment, the period of time can be up to about 24 hours.

The method of the present disclosure further comprises detecting a colony of an aerobic or aerotolerant bacterium in the culture device (e.g., observing an aerobic and/or aerotolerant bacterial colony in the culture device). In any embodiment, detecting an aerobic and/or aerotolerant bacterial colony in the culture device can comprise detecting in the culture device a presence or an absence of the detectable reporter group of at least one of the indicator agents, wherein detecting the presence of the detectable reporter group is indicative of a presence of aerobic and/or aerotolerant bacteria. As a colony of aerobic and/or aerotolerant bacteria grows in the culture device of the present disclosure, the cells in the colony react with one or more of the indicator agents to activate (e.g., by hydrolysis of a chromogenic or fluorogenic enzyme substrate) the reporter group thereby directly or indirectly making the reporter group detectable. In the case of chromogenic indicator agents, the reporter group can be detected by the characteristic wavelengths of light that it absorbs and/or reflects. For example, indicator agents comprising an indolyl reporter group can dimerize to form indigo or derivatives thereof. Thus, the presence of a colony having a color (e.g., either the colony having the color or the hydrogel proximate the colony having the color) that is associated with a particular reporter group is indicative of a colony of aerobic and/or aerotolerant bacteria.

In the case of fluorogenic indicator agents, the detectable reporter group can be observed by illuminating the culture device with an appropriate wavelength of light (e.g., about 365 nm to detect a reporter group comprising 4-methylumbelliferone) and observing the light emitted by the reporter group. A person having ordinary skill in the art will recognize suitable wavelengths of light required respectively to illuminate the culture device and to detect a reporter group associated with a particular fluorogenic indicator agent. A colony having the color of the fluorescent reporter group or the presence of the fluorescent reporter group in the hydrogel proximate the colony is in indication the colony comprises aerobic and/or aerotolerant bacteria.

In any embodiment, detecting the reporter group can comprise observing the culture device visually. In any embodiment, detecting the reporter group can comprise obtaining an image of the culture device and observing the image visually or analyzing the image using automated image-analysis techniques. Methods and devices for automated detection of microbial colonies in a culture device are described, for example, in U.S. Pat. Nos. 5,448,652; 6,058, 209; 6,243,486; 6,271,022; 7,298,885; and 7,319,031; which are all incorporated herein by reference in their entirety.

In any embodiment, the method of the present disclosure further comprises enumerating colonies of aerobic and/or aerotolerant bacteria present in the inoculated culture device after incubating the inoculated culture device. Thus, after the colonies of aerobic and/or aerotolerant bacteria are detected as described herein, the number of detected colonies is determined either manually or using automated processes known in the art.

Exemplary Embodiments

Embodiment A is a device for culturing and detecting microorganisms, the device comprising:
a self-supporting substrate sheet having a first major surface and a second major surface;
a cover sheet attached to the substrate sheet;
a sample-receiving zone disposed between the substrate sheet and the cover sheet;
a first layer comprising a substantially dry, cold-water-soluble first hydrogel-forming composition adhered to the first major surface of the substrate sheet; and
a plurality of indicator agents, the plurality of indicator agents comprising:
three indicator agents for detecting distinct glycosidase enzyme activities;
an indicator agent for detecting an alkyl esterase enzyme activity;
an indicator agent for detecting a phosphatase enzyme activity;
a redox indicator comprising a tetrazolium dye;
wherein each of the plurality of indicator agents comprises a detectable reporter group;
wherein each of the plurality of indicator agents is disposed in at least one layer adhered to the substrate sheet or the cover sheet, wherein the at least one layer is in fluid communication with the sample-receiving zone when a predetermined volume of aqueous liquid is deposited in the sample-receiving zone.

Embodiment B is the device of Embodiment A, further comprising a second layer comprising a first adhesive composition disposed between the substrate sheet and the first layer.

Embodiment C is the device of Embodiment A or Embodiment B, further comprising an air-permeable membrane adhered to the substrate sheet.

Embodiment D is the device of Embodiment C, wherein the air-permeable membrane is disposed between the substrate sheet and the first layer.

Embodiment E is the device of Embodiment C, wherein the air-permeable membrane is substantially opaque.

Embodiment F is the device of Embodiment C or Embodiment D, wherein the air-permeable membrane is substantially free of visible indicia.

Embodiment G is the device of any one of the preceding Embodiments, wherein the first hydrogel-forming composition further comprises a nutrient to facilitate growth of an aerobic bacterium, wherein the first hydrogel-forming composition is adhered to at least a portion of the substrate sheet or the cover sheet, wherein the portion is in fluid communication with the sample-receiving zone.

Embodiment H is the device of any one of the preceding Embodiments, wherein the cover sheet comprises a first major surface, wherein the first major surface of the cover sheet faces the first major surface of the substrate sheet, wherein the culture device further comprises:
a third layer comprising a second adhesive composition, wherein the third layer is adhered to a portion of the cover sheet; and
a fourth layer comprising a substantially dry, cold-water-soluble second hydrogel-forming composition, wherein the fourth layer is adhered to the third layer.

Embodiment I is the device of any one of the preceding Embodiments, wherein at least one of the plurality of indicator agents is disposed in the first adhesive composition, the second adhesive composition, the first hydrogel-forming composition, and/or the second hydrogel-forming composition.

Embodiment J is the device of Embodiment I, wherein at least three indicator agents of the plurality of indicator agents are disposed in the first adhesive composition and/or the second adhesive composition.

Embodiment K is the device of any one of the preceding Embodiments, wherein the first hydrogel-forming composition, and/or the second hydrogel-forming composition comprises a mixture of gelling agents.

Embodiment L is the device of Embodiment K, wherein the mixture of gelling agents comprises xanthan gum and guar gum in a mass ratio of about 1:1.

Embodiment M is the device of any one of the preceding Embodiments, wherein the at least three enzyme activity indicator reagents for detecting distinct glycosidase enzyme activities include a compound to detect alpha-glucosidase enzyme activity, a compound to detect beta-glucosidase enzyme activity, and a compound to detect beta-galactosidase enzyme activity.

Embodiment N is the device of Embodiment M, wherein the at least three enzyme activity indicator reagents for detecting distinct glycosidase enzyme activities comprise 5-bromo-4-chloro-3-indolyl-beta-D-galactopyranoside or a salt thereof, 5-bromo-4-chloro-3-indolyl-alpha-D-glucopyranoside or a salt thereof, and 5-bromo-4-chloro-3-indolyl-beta-D-glucopyranoside or a salt thereof.

Embodiment O is the device of any one of the preceding Embodiments, wherein the enzyme activity indicator reagent for detecting an alkyl esterase enzyme activity comprises 3-indolyl-acetate or a salt thereof.

Embodiment P is the device of any one of the preceding claims, wherein the enzyme activity indicator reagent for detecting a phosphatase enzyme activity comprises 5-bromo-4-chloro-3-indolyl-phosphate or a salt thereof.

Embodiment Q is the device of any one of the preceding Embodiments, further comprising a water-insoluble spacer having an aperture, the spacer being attached to the substrate sheet or the cover sheet and the aperture being positioned between the substrate sheet and the cover sheet, wherein the aperture defines a peripheral boundary of the sample-receiving zone.

Embodiment R is the device of Embodiment Q, wherein the spacer comprises a thickness; wherein the thickness is dimensioned to space apart the cover sheet or any layer adhered thereto from a predetermined volume of aqueous liquid deposited into the sample-receiving zone.

Embodiment S is the device of any one of the preceding Embodiments, further comprising a predefined volume of aqueous liquid disposed between the substrate sheet and the cover sheet in the sample receiving zone.

Embodiment T is the device of any one of the preceding Embodiments, wherein the first hydrogel-forming composition or second hydrogel-forming composition further comprises an effective amount of at least one nutrient for growing an aerobic bacterium.

Embodiment U is the device of Embodiment T, wherein the at least one nutrient is selected from the group consisting of Soytone, meat peptone, Tryptone, yeast extract, pyruvic acid, or a combination of any two or more of the foregoing nutrients.

Embodiment V is the device of any one of the preceding Embodiments, further comprising a nutrient selected from the group consisting of L-arginine, skim milk, D-trehalose, and a combination of any two or more of the foregoing nutrients.

Embodiment W is the device of any one of the preceding Embodiments, wherein the first hydrogel-forming composition or the second hydrogel-forming composition comprises substantially dry agglomerated powders.

Embodiment X is a method of detecting an aerobic bacterium in a sample, the method comprising:

contacting a sample material and an aqueous liquid in the sample-receiving zone of the device of any one of Embodiments A through W to form an inoculated culture device;

incubating the inoculated culture device for a period of time; and detecting a bacterial colony in the inoculated culture device.

Embodiment Y is the method of Embodiment X, wherein detecting a bacterial colony in the inoculated culture device comprises detecting in the inoculated culture device a presence of a formazan dye or the detectable reporter group of at least one of the indicator agents, wherein detecting the presence of the formazan dye or the detectable reporter group is indicative of a presence of a colony of bacteria.

Embodiment Z is the method of Embodiment X or Embodiment Y, wherein contacting a sample material with the first hydrogel-forming composition or second hydrogel-forming composition of the device comprises placing the sample in fluid communication with a nutrient to facilitate growth of an aerobic bacterium.

Embodiment AA is the method of any one of Embodiments X through Z, wherein incubating the inoculated culture device comprises incubating the inoculated culture device at a temperature between about 25° C. and about 42° C., inclusive.

Embodiment BB is the method of any one of Embodiments X through AA, wherein incubating the inoculated culture device for a period of time comprises incubating the inoculated culture device for about 22 hours to about 26 hours, inclusive.

Embodiment CC is the method of any one of Embodiments X through BB, further comprising enumerating aerobic bacteria colonies present in the inoculated culture device after incubating the inoculated culture device.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

Examples

Indicators

The indicator agents that were used in the examples are listed in Table 6.

TABLE 6

| Indicator Name | CAS Number | Source |
| --- | --- | --- |
| 5-Bromo-4-chloro-3-indolyl acetate (X-3-Acetate) | 3252-36-6 | Biosynth International, (Itasca, IL) |
| 5-Bromo-4-chloro-3-indolyl-beta-D-galactopyranoside (X-Gal) | 7240-90-6 | Biosynth International |

TABLE 6-continued

| Indicator Name | CAS Number | Source |
| --- | --- | --- |
| 5-Bromo-4-chloro-3-indolyl-beta-D-glucopyranoside (X-β-Glu) | 15548-60-4 | Biosynth International |
| 5-Bromo-4-chloro-3-indolyl-alpha-D-glucopyranoside (X-α-Glu) | 108789-36-2 | Biosynth International |
| 5-Bromo-4-chloro-3-indolyl phosphate para-toluidine salt (BCIP p-toluidine) | 6578-06-9 | Biosynth International |
| Triphenyltetrazolium chloride | 298-96-4 | Sigma-Aldrich (St. Louis, MO) |

Culture Media Formulations

Each culture medium formulation was prepared as a homogeneous mixture by blending the formulation ingredients together. The contents of the culture media formulations used in the examples are described in Tables 7-8

TABLE 7

Culture Medium Formulation A (for Example 1)

| Ingredient | Amount (grams) | Source |
| --- | --- | --- |
| Meat peptone, porcine | 3.0 | Alpha Biosciences (Baltimore, MD) |
| Soytone | 3.0 | Becton, Dickinson (New Franklin, NJ) |
| Tryptone | 3.0 | Becton, Dickinson (New Franklin, NJ) |
| Yeast extract | 6.0 | Alpha Biosciences (Baltimore, MD) |
| Pyruvic acid (sodium salt) | 18.5 | J. T. Baker (Center Valley, PA) |
| Potassium phosphate monobasic | 1.2 | EMD Millipore (Billerica, MA) |
| Potassium phosphate dibasic | 3.6 | EMD Millipore (Billerica, MA) |
| Dextrose | 1.5 | Becton, Dickinson (New Franklin, NJ) |
| Magnesium sulfate | 0.1 | EMD Millipore (Billerica, MA) |
| Calcium chloride | 0.1 | Mallinckrodt (St. Louis, MO) |
| Magnesium chloride | 0.1 | Alfa Aesar (Ward Hill, MA) |
| Sodium carbonate | 0.1 | Sigma-Aldrich (St. Louis, MO) |
| Zinc sulfate | 0.1 | EMD Millipore (Billerica, MA) |
| L-Arginine hydrochloride | 0.26 | EMD Millipore (Billerica, MA) |
| D-(+)-Trehalose | 0.5 | Alfa Aesar (Ward Hill, MA) |
| Skim milk powder | 0.5 | EMD Millipore (Billerica, MA) |
| Total Ingredients | 41.56 | |

TABLE 8

Culture Medium Formulation B (for Examples 2-5)

| Ingredient | Amount (grams) | Source |
| --- | --- | --- |
| Meat peptone, porcine | 2.2 | Alpha Biosciences (Baltimore, MD) |
| Soytone | 2.2 | Becton, Dickinson (New Franklin, NJ) |
| Tryptone | 2.2 | Becton, Dickinson (New Franklin, NJ) |
| Yeast extract | 4.8 | Alpha Biosciences (Baltimore, MD) |
| Pyruvic acid (sodium salt) | 14 | J. T. Baker (Center Valley, PA) |
| Potassium phosphate monobasic | 0.8 | EMD Millipore (Billerica, MA) |
| Potassium phosphate dibasic | 2.6 | EMD Millipore (Billerica, MA) |
| Dextrose | 1.2 | Becton, Dickinson (New Franklin, NJ) |
| Magnesium sulfate, hydrate | 3 | EMD Millipore (Billerica, MA) |

TABLE 8-continued

Culture Medium Formulation B (for Examples 2-5)

| Ingredient | Amount (grams) | Source |
|---|---|---|
| L-Arginine hydrochloride | 0.07[a] | EMD Millipore (Billerica, MA) |
| L-Arginine hydrochloride | 0.21[b] | |
| Total Ingredients | 33.07[a]/ 33.21[b] | |

[a]Examples 4 and 5.
[b]Examples 2 and 3.

Inoculation and Incubation

The bacterial strains were purchased as KWIK STIK™ devices from MicroBiologics, Inc. (St. Cloud, Minn.) or were natural isolates from food or clinical samples. The bacteria were propagated from the KWIK STIK devices per manufacturer's instructions by isolation onto Tryptic Soy Agar medium. Following isolation, individual colonies were transferred into 5 ml sterile Tryptic Soy Broth and incubated for 24 hours at the appropriate temperature The samples of overnight cultures were each serially diluted in Butterfield's Buffer water to yield concentrations that provided counts of colony forming units (cfu) within the counting range of the thin film culture device (approximately 15-300 cfu per device).

TABLE 9

Bacterial Strain Set A (used in Example 1)

*Escherichia coli* (ATCC 51813)
*Staphylococcus aureus* (ATCC 25923)
*Pseudomonas aeruginosa* (ATCC 35032)
*Enterococcus faecalis* (ATCC 29212)
*Bacillus spizizenii* (ATCC 6633)
*Microbacterium esteraromaticum*
*Streptococcus agalactiae* (ATCC27956)
*Proteus vulgaris* (ATCC 13315)
*Kocuria* spp.
*Streptococcus cremoris* (ATCC19247)

TABLE 10

Bacterial Strain Set B (used in Examples 2-5)

*Pseudomonas flourescens* (ATCC 17386)
*Bacillus cereus* (ATCC 10876)
*Bacillus licheniformis* (ATCC 14580)
*Bacillus spizizenii* (ATCC 6633)
*Enterococcus faecalis* (ATCC 29212)
*Pseudomonas aeruginosa* (ATCC 27853)
*Pseudomonas putida* (ATCC 49128)
*Proteus vulgaris* (ATCC 13315)
*Microbacterium esteraromaticum*
*Streptococcus cremoris* (ATCC 19247)
*Pseudomonas* spp.
*Alcaligenes faecalis* (ATCC 35655)

Standard Methods Agar (SMA) plates were prepared as follows: The SMA medium (23.5 g; obtained from Becton Dickinson; New Franklin, N.J.) was suspended in 1 L of purified water and autoclaved. The sterile SMA was tempered to 48+/−2° C. prior to use. A 1 mL aliquot of the inoculum each was added to a sterile Petri dishes in duplicate and 12-15 ml of SMA medium (previously tempered to 48+/−2° C.) was added. The Petri dish was swirled gently to ensure mixing of the agar with the inoculum ients and then incubated at 32° C. for 48 hours. The colonies in each device were counted by visual examination at the end of the incubation period. The cfu counts of the individual devices were averaged and the average count value was determined.

Culture Devices

The thin film culture devices were prepared using the general procedures described in U.S. Pat. Nos. 4,565,783 and 5,089,413. The specific details for the preparation of various thin film culture devices are described in Examples 1-5. Xanthan gum and guar gum were obtained from the Sigma-Aldrich Company).

Example 1. Preparation of a Detection Device (Having a Microporous Film, a Plurality of Indicator Agents, and a Blend of Gelling Agents) for Detection and Enumeration of Aerobic Bacteria A first coating formulation (containing TTC and a pressure-sensitive adhesive (i.e., the isooctylacrylate/acrylic acid adhesive described in Example 1 of U.S. Pat. No. 5,601,998; which is incorporated herein by reference in its entirety)) for the cover sheet of the thin film culture device was prepared and coated onto a biaxially-oriented polypropylene (BOPP) film as described in Example 11 of U.S. Pat. No. 4,565,783, which is incorporated by reference in its entirety. The adhesive-coated side of the BOPP film was then powder coated with a pre-blended 1:1 mixture of guar gum and xanthan gum. The powder was evenly applied and excess powder was removed from the adhesive layer by hand shaking of the film.

The indicator coating formulation for the substrate sheet contained the five chromogenic substrate (indolyl) indicators listed in Table 6. The indicators were dissolved in a suitable polar solvent. The resulting formulation was stirred until homogeneous. The homogeneous mixture of indicators in the solvent was added to the same pressure-sensitive adhesive (i.e., an isooctylacrylate/acrylic acid adhesive) used to make the first coating formulation (above) to obtain the final concentrations of each indicator shown in Table 11.

TABLE 11

Composition of adhesive with chromogenic enzyme substrates.

| Indicator Name | grams indicator/ Kg of adhesive |
|---|---|
| 5-Bromo-4-chloro-3-indolyl acetate (X-3-Acetate) | 0.56 |
| 5-Bromo-4-chloro-3-indolyl-beta-D-galactopyranoside (X-Gal) | 1.24 |
| 5-Bromo-4-chloro-3-indolyl-beta-D-glucopyranoside (X-β-Glu) | 1.24 |
| 5-Bromo-4-chloro-3-indolyl-alpha-D-glucopyranoside (X-α-Glu) | 1.24 |
| 5-Bromo-4-chloro-3-indolyl phosphate para-toluidine salt (BCIP p-toluidine) | 1.24 |

The culture medium coating formulation was prepared by combining the pre-blended Culture Medium Formulation A (described in Table 7), water (1 L), and a blend of 12 g of a xanthan gum and guar gum (1:1 by weight) mixture. The resulting mixture was heated to 80° C. with stirring. The mixture was cooled to room temperature and stored in a refrigerator until used to coat the substrate sheet.

The substrate sheet of the thin film culture device was prepared using a hydrophobic paper (a bleached kraft paper coated with a water-resistance polymeric layer). A sheet of microporous polypropylene film (APTRA Classic film; approximately 38 μm thick, approximately 25 g/m basis weight; available from RKW Danafilms, Westborough, Mass.) was press-laminated against the adhesive coated paper. The indicator formulation containing the indolyl indicators of Table 11 mixed into the pressure-sensitive adhesive was knife coated (gap setting of about 0.1 mm)-onto the microporous film attached to the substrate sheet and the coated laminate was allowed to dry in air.

The chilled culture medium coating formulation was then knife coated onto the dried indicator formulation layer (gap setting about 0.3 mm) The resulting coated laminate was dried in an oven at 93-104° C. for 1-20 minutes. The coated, dried laminate was cut into 76 mm wide by 102 mm long sections that formed the substrate sheet of the device. A foam spacer (polystyrene foam; 76 mm wide by 102 mm long by 0.57 mm thick) with a circular opening (61 mm in diameter) was adhesively laminated to the coated side of the substrate sheet. The circular opening was positioned near the center of the foam layer and defined the growth zone of the device.

As illustrated in FIGS. 4-6, the thin film culture device was assembled by attaching the cover sheet (which was cut to match the size of the substrate sheet) to the substrate sheet along one edge using a double sided adhesive tape. The cover sheet and substrate sheet of each device were oriented so that the coated surfaces were facing each other.

The thin film culture devices were inoculated with a single microbial sample selected from Escherichia coli, Stapylococcus aureus, Pseudomonas aeruginosa, Enterococcus faecalis, Bacillus spizizenii, Microbacterium esteraromaticum, Streptococcus agalactiae, Proteus vulgaris, Kocuria spp., Streptococcus cremoris (Bacterial Strain Set A, Table 9). The cover sheet of the device was lifted and 1 mL of the inoculum was added (by pipet) to the culture medium on the substrate sheet. The cover sheet was replaced and the sample was uniformly spread to the edges of the circular opening by applying downward pressure with a 3M PETRIFILM Flat Spreader (3M Company, St. Paul, Minn.). Duplicate thin film culture devices were prepared for each sample. Inoculated devices were incubated at 32° C. for 24 hours or 35° C. for 24 hours.

The colonies in each device were counted by visual examination at the end of the incubation period (24 hour time point). All colonies within the circular growth were counted regardless of color. The cfu counts of the individual devices were averaged and the average count value was determined.

The colonies on reference SMA plates were counted in the same manner as described for the thin film culture devices. The cfu counts for the SMA plates were taken after 48 hours of incubation. The results are presented in Table 12.

TABLE 12

| | Average Colony Count (cfu) | | |
|---|---|---|---|
| | Example 1 32° C. for 24 hours | Example 1 35° C. for 24 hours | SMA Reference Plate 32° C. for 48 hours |
| Escherichia coli | 383 | 364 | 393 |
| Staphylococcus aureus | 445 | 540 | 550 |
| Pseudomonas aeruginosa | 238 | 167 | 315 |
| Enterococcus faecalis | 161 | 144 | 155 |
| Bacillus spizizenii | 13 | 10 | 8 |
| Microbacterium esteraromaticum | 221 | 194 | 220 |

TABLE 12-continued

| | Average Colony Count (cfu) | | |
|---|---|---|---|
| | Example 1 32° C. for 24 hours | Example 1 35° C. for 24 hours | SMA Reference Plate 32° C. for 48 hours |
| Streptococcus agalactiae | 37 | 32 | 27 |
| Proteus vulgaris | 235 | 222 | 225 |
| Kocuria spp. | 158 | 155 | 166 |
| Streptococcus cremoris | 203 | 194 | 181 |

Example 2. Preparation of a Detection Device (Having a Plurality of Indicator Agents, and a Blend of Gelling Agents) for Detection and Enumeration of Aerobic Bacteria A first coating formulation (containing TTC and a pressure-sensitive adhesive (i.e., the isooctylacrylate/acrylic acid adhesive described in Example 1 of U.S. Pat. No. 5,601,998; which is incorporated herein by reference in its entirety)) for the cover sheet of the thin film culture device was prepared and coated onto a biaxially-oriented polypropylene (BOPP) film as described in Example 11 of U.S. Pat. No. 4,565,783, which is incorporated by reference in its entirety. The adhesive-coated side of the BOPP film was then powder coated with a pre-blended 1:1 mixture of guar gum and xanthan gum. The powder was evenly applied and excess powder was removed from the adhesive layer by hand shaking of the film.

The indicator coating formulation, containing chromogenic enzyme substrates and a pressure-sensitive adhesive, was prepared as described in Example 1.

The culture medium coating formulation was prepared by combining the pre-blended Culture Medium Formulation B (described in Table 8), water (1 L), and a blend of 12 g of a xanthan gum and guar gum (1:1 by weight) mixture. The resulting mixture was heated to 80° C. with stirring. The mixture was cooled to room temperature and stored in a refrigerator until used to coat the substrate sheet. The mixture was cooled to room temperature and stored in a refrigerator until used to coat the substrate sheet.

The substrate sheet of the thin film culture device was prepared using a hydrophobic paper (a bleached kraft paper coated with a water-resistance polymeric layer). The indicator formulation containing the indolyl indicators of Table 11 mixed into the pressure-sensitive adhesive was knife coated (gap setting of about 0.1 mm)-onto the substrate sheet and the coated substrate sheet was allowed to dry in air.

The chilled culture medium coating formulation was then knife coated onto the dried indicator formulation layer (gap setting about 0.3 mm) The resulting coated laminate was dried in an oven at 93-104° C. for 1-20 minutes. The coated, dried laminate was cut into 76 mm wide by 102 mm long sections that formed the substrate sheet of the device. A foam spacer (polystyrene foam; 76 mm wide by 102 mm long by 0.57 mm thick) with a circular opening (51 mm in diameter) was adhesively laminated to the coated side of the substrate sheet. The circular opening was positioned near the center of the foam layer and defined the growth zone of the device.

As illustrated in FIGS. 1-2, the thin film culture device was assembled by attaching the cover sheet (which was cut to match the size of the substrate sheet) to the substrate sheet along one edge using a double sided adhesive tape. The cover sheet and substrate sheet of each device were oriented so that the coated surfaces were facing each other.

The thin film culture devices were inoculated with a single microbial sample selected from Bacterial Strain Set B (Table 10). The cover sheet of the device was lifted and 1 mL of the inoculum was added (by pipet) to the culture medium on the substrate sheet. The cover sheet was replaced and the sample was uniformly spread to the edges of the circular opening by applying downward pressure with a 3M PETRIFILM Flat Spreader (3M Company, St. Paul, Minn.). Inoculated devices were incubated at 32° C. for 24 hours.

The colonies in each device were counted by visual examination at the end of the incubation period (24 hour time point). All colonies within the circular growth were counted regardless of color.

3M PETRIFILM Aerobic Count plates ("PETRIFILM AC plates"; 3M Corporation, St. Paul, Minn.) were used as reference culturing devices. The PETRIFILM AC plates were inoculated and counted in the same manner as described for the thin film culture devices. However, the PETRIFILM AC plates were incubated at 32° C. for 48 hours. The results are presented in Table 13.

Example 3 Preparation of a Detection Device
(Having a Microporous Film, a Plurality of
Indicator Agents, and a Blend of Gelling Agents)
for Detection and Enumeration of Aerobic Bacteria A first coating formulation (containing TTC and a pressure-sensitive adhesive (i.e., the isooctylacrylate/acrylic acid adhesive described in Example 1 of U.S. Pat. No. 5,601,998; which is incorporated herein by reference in its entirety)) for the cover sheet of the thin film culture device was prepared and coated onto a biaxially-oriented polypropylene (BOPP) film as described in Example 11 of U.S. Pat. No. 4,565,783, which is incorporated by reference in its entirety. The adhesive-coated side of the BOPP film was then powder coated with a pre-blended 1:1 mixture of guar gum and xanthan gum. The powder was evenly applied and excess powder was removed from the adhesive layer by hand shaking of the film.

The indicator coating formulation, containing chromogenic enzyme substrates and a pressure-sensitive adhesive, was prepared as described in Example 1.

The culture medium coating formulation was prepared by combining the pre-blended Culture Medium Formulation B (described in Table 8), water (1 L), and a blend of 12 g of a xanthan gum and guar gum (1:1 by weight) mixture. The resulting mixture was heated to 80° C. with stirring. The mixture was cooled to room temperature and stored in a refrigerator until used to coat the substrate sheet. The mixture was cooled to room temperature and stored in a refrigerator until used to coat the substrate sheet.

The substrate sheet of the thin film culture device was prepared using a hydrophobic paper (a bleached kraft paper coated with a water-resistance polymeric layer). A sheet of microporous polypropylene film (APTRA Classic film; approximately 38 μm thick, approximately 25 g/m basis weight; available from RKW Danafilms, Westborough, Mass.) was press-laminated against the adhesive coated paper. The indicator formulation containing the indolyl indicators of Table 11 mixed into the pressure-sensitive adhesive was knife coated (gap setting of about 0.1 mm)- onto the microporous film attached to the substrate sheet and the coated laminate was allowed to dry in air.

The chilled culture medium coating formulation was then knife coated onto the dried indicator formulation layer (gap setting about 0.3 mm) The resulting coated laminate was dried in an oven at 93-104° C. for 1-20 minutes. The coated, dried laminate was cut into 76 mm wide by 102 mm long sections that formed the substrate sheet of the device. A foam spacer (polystyrene foam; 76 mm wide by 102 mm long by 0.57 mm thick) with a circular opening (51 mm in diameter) was adhesively laminated to the coated side of the substrate sheet. The circular opening was positioned near the center of the foam layer and defined the growth zone of the device.

As illustrated in FIGS. 4-6, the thin film culture device was assembled by attaching the cover sheet (which was cut to match the size of the substrate sheet) to the substrate sheet along one edge using a double sided adhesive tape. The cover sheet and substrate sheet of each device were oriented so that the coated surfaces were facing each other.

The thin film culture devices were inoculated with a single microbial sample selected from Bacterial Strain Set B (Table 10). The cover sheet of the device was lifted and 1 mL of the inoculum was added (by pipet) to the culture medium on the substrate sheet. The cover sheet was replaced and the sample was uniformly spread to the edges of the circular opening by applying downward pressure with a 3M PETRIFILM Flat Spreader (3M Company, St. Paul, Minn.). Inoculated devices were incubated at 32° C. for 24 hours.

The colonies in each device were counted by visual examination at the end of the incubation period (24 hour time point). All colonies within the circular growth were counted regardless of color.

PETRIFILM AC plates were used as reference culturing devices. The PETRIFILM AC plates were inoculated and counted in the same manner as described for the thin film culture devices. However, the PETRIFILM AC plates were incubated at 32° C. for 48 hours. The results are presented in Table 13.

Example 4 Preparation of a Detection Device
(Having a Plurality of Indicator Agents) for
Detection and Enumeration of Aerobic Bacteria A first coating formulation (containing TTC and a pressure-sensitive adhesive (i.e., the isooctylacrylate/acrylic acid adhesive described in Example 1 of U.S. Pat. No. 5,601,998; which is incorporated herein by reference in its entirety)) for the cover sheet of the thin film culture device was prepared and coated onto a biaxially-oriented polypropylene (BOPP) film as described in Example 11 of U.S. Pat. No. 4,565,783, which is incorporated by reference in its entirety. The adhesive-coated side of the BOPP film was then powder coated with guar gum. The powder was evenly applied and excess powder was removed from the adhesive layer by hand shaking of the film.

The indicator coating formulation, containing chromogenic enzyme substrates and a pressure-sensitive adhesive, was prepared as described in Example 1.

The culture medium coating formulation was prepared by combining the pre-blended Culture Medium Formulation B (described in Table 8), water (1 L), and 12 g of guar gum. The resulting mixture was heated to 80° C. with stirring. The mixture was cooled to room temperature and stored in a refrigerator until used to coat the substrate sheet. The mixture was cooled to room temperature and stored in a refrigerator until used to coat the substrate sheet.

The substrate sheet of the thin film culture device was prepared using a hydrophobic paper (a bleached kraft paper coated with a water-resistance polymeric layer). The indicator formulation containing the indolyl indicators of Table 11 mixed into the pressure-sensitive adhesive was knife coated (gap setting of about 0.1 mm)-onto the substrate sheet and the coated substrate sheet was allowed to dry in air.

The chilled culture medium coating formulation was then knife coated onto the dried indicator formulation layer (gap setting about 0.3 mm) The resulting coated laminate was dried in an oven at 93-104° C. for 1-20 minutes. The coated, dried laminate was cut into 76 mm wide by 102 mm long sections that formed the substrate sheet of the device. A foam spacer (polystyrene foam; 76 mm wide by 102 mm long by 0.57 mm thick) with a circular opening (51 mm in diameter) was adhesively laminated to the coated side of the substrate sheet. The circular opening was positioned near the center of the foam layer and defined the growth zone of the device.

As illustrated in FIGS. 1-2, the thin film culture device was assembled by attaching the cover sheet (which was cut to match the size of the substrate sheet) to the substrate sheet along one edge using a double sided adhesive tape. The cover sheet and substrate sheet of each device were oriented so that the coated surfaces were facing each other.

The thin film culture devices were inoculated with a single microbial sample selected from Bacterial Strain Set B (Table 10). The cover sheet of the device was lifted and 1 mL of the inoculum was added (by pipet) to the culture medium on the substrate sheet. The cover sheet was replaced and the sample was uniformly spread to the edges of the circular opening by applying downward pressure with a 3M PETRIFILM Flat Spreader (3M Company, St. Paul, Minn.). Inoculated devices were incubated at 32° C. for 24 hours.

The colonies in each device were counted by visual examination at the end of the incubation period (24 hour time point). All colonies within the circular growth were counted regardless of color.

3M PETRIFILM Aerobic Count plates ("PETRIFILM AC plates"; 3M Corporation, St. Paul, Minn.) were used as reference culturing devices. The PETRIFILM AC plates were inoculated and counted in the same manner as described for the thin film culture devices. However, the PETRIFILM AC plates were incubated at 32° C. for 48 hours. The results are presented in Table 13.

Example 5 Preparation of a Detection Device (Having a Microporous Film and a Plurality of Indicator Agents) for Detection and Enumeration of Aerobic Bacteria A first coating formulation (containing TTC and a pressure-sensitive adhesive (i.e., the isooctylacrylate/acrylic acid adhesive described in Example 1 of U.S. Pat. No. 5,601,998; which is incorporated herein by reference in its entirety)) for the cover sheet of the thin film culture device was prepared and coated onto a biaxially-oriented polypropylene (BOPP) film as described in Example 11 of U.S. Pat. No. 4,565,783, which is incorporated by reference in its entirety. The adhesive-coated side of the BOPP film was then powder coated with guar gum. The powder was evenly applied and excess powder was removed from the adhesive layer by hand shaking of the film.

The indicator coating formulation, containing chromogenic enzyme substrates and a pressure-sensitive adhesive, was prepared as described in Example 1.

The culture medium coating formulation was prepared by combining the pre-blended Culture Medium Formulation B (described in Table 8), water (1 L), and 12 g of guar gum. The resulting mixture was heated to 80° C. with stirring. The mixture was cooled to room temperature and stored in a refrigerator until used to coat the substrate sheet. The mixture was cooled to room temperature and stored in a refrigerator until used to coat the substrate sheet.

The substrate sheet of the thin film culture device was prepared using a hydrophobic paper (a bleached kraft paper coated with a water-resistance polymeric layer). A sheet of microporous polypropylene film (APTRA Classic film; approximately 38 μm thick, approximately 25 g/m basis weight; available from RKW Danafilms, Westborough, Mass.) was press-laminated against the adhesive coated paper. The indicator formulation containing the indolyl indicators of Table 11 mixed into the pressure-sensitive adhesive was knife coated (gap setting of about 0.1 mm)-onto the microporous film attached to the substrate sheet and the coated laminate was allowed to dry in air.

The chilled culture medium coating formulation was then knife coated onto the dried indicator formulation layer (gap setting about 0.3 mm) The resulting coated laminate was dried in an oven at 93-104° C. for 1-20 minutes. The coated, dried laminate was cut into 76 mm wide by 102 mm long sections that formed the substrate sheet of the device. A foam spacer (polystyrene foam; 76 mm wide by 102 mm long by 0.57 mm thick) with a circular opening (51 mm in diameter) was adhesively laminated to the coated side of the substrate sheet. The circular opening was positioned near the center of the foam layer and defined the growth zone of the device.

As illustrated in FIGS. 4-6, the thin film culture device was assembled by attaching the cover sheet (which was cut to match the size of the substrate sheet) to the substrate sheet along one edge using a double sided adhesive tape. The cover sheet and substrate sheet of each device were oriented so that the coated surfaces were facing each other.

The thin film culture devices were inoculated with a single microbial sample selected from Bacterial Strain Set B (Table 10). The cover sheet of the device was lifted and 1 mL of the inoculum was added (by pipet) to the culture medium on the substrate sheet. The cover sheet was replaced and the sample was uniformly spread to the edges of the circular opening by applying downward pressure with a 3M PETRIFILM Flat Spreader (3M Company, St. Paul, Minn.). Inoculated devices were incubated at 32° C. for 24 hours.

The colonies in each device were counted by visual examination at the end of the incubation period (24 hour time point). All colonies within the circular growth were counted regardless of color.

3M PETRIFILM Aerobic Count plates ("PETRIFILM AC plates"; 3M Corporation, St. Paul, Minn.) were used as reference culturing devices. The PETRIFILM AC plates were inoculated and counted in the same manner as described for the thin film culture devices. However, the PETRIFILM AC plates were incubated at 32° C. for 48 hours. The results are presented in Table 13.

TABLE 13

Colony count results.

| | Average Colony Count (cfu) | | | | |
|---|---|---|---|---|---|
| | Example 2 | Example 3 | Example 4 | Example 5 | 3M PETRIFILM AC Plate (Reference) |
| Pseudomonas flourescens | 70 | 88 | 78 | 87 | 88 |
| Bacullus cereus | 18 | 24 | 27 | 30 | 13 |
| Bacillus licheniformis | 56 | 56 | 42 | 50 | 61 |
| Bacillus spizizenii | 43 | 42 | 43 | 33 | 34 |
| Enterococcus faecalis | 12 | 20 | 15 | 14 | 11 |
| Pseudomonas aeruglinosa | 193 | 245 | 225 | 234 | 282 |
| Pseudomonas putida | 27 | 42 | 21 | 38 | 38 |
| Proteus vulgaris | 54 | 137 | 64 | 87 | 78 |
| Microbacterium esteraromaticum | 18 | 24 | 13 | 19 | 21 |
| Streptococcus cremoris | 2 | 18 | 4 | 11 | 0 |
| Pseudomonas spp. | 15 | 49 | 13 | 40 | 45 |
| Alkaligenes faecalis | 32 | 74 | 53 | 80 | 92 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of detecting an aerobic bacterium in a sample, the method comprising:
    contacting a sample material and an aqueous liquid in the sample-receiving zone of a device, the device comprising a self-supporting substrate sheet having a first major surface and a second major surface;
    a cover sheet attached to the substrate sheet;
    a sample-receiving zone disposed between the substrate sheet and the cover sheet;
    a first layer comprising a substantially dry, cold-water-soluble first hydrogel-forming composition adhered to the first major surface of the substrate sheet, the substantially dry, cold-water-soluble first hydrogel-forming composition comprising guar gum and xanthan gum in a weight ratio of about 1:1; and
    a plurality of indicator agents, the plurality of indicator agents comprising:
        three enzyme activity indicator reagents for detecting distinct glycosidase enzyme activities;
        an enzyme activity indicator reagent for detecting an alkyl esterase enzyme activity;
        an enzyme activity indicator reagent for detecting a phosphatase enzyme activity; and
        a redox indicator comprising a tetrazolium dye;
    wherein each of the plurality of enzyme activity indicator reagents comprises a detectable reporter group;
    wherein each of the plurality of indicator agents is disposed in at least one layer adhered to the substrate sheet or the cover sheet, wherein the at least one layer is in fluid communication with the sample-receiving zone when a predetermined volume of aqueous liquid is deposited in the sample-receiving zone to form an inoculated culture device;
    incubating the inoculated culture device for a period of time; and
    detecting a bacterial colony from genera *Bacillus* in the inoculated culture device.

2. The method of claim 1, wherein detecting a bacterial colony in the inoculated culture device comprises detecting in the inoculated culture device a presence of a formazan dye or the detectable reporter group of at least one of the indicator agents, wherein detecting the presence of the formazan dye or the detectable reporter group is indicative of a presence of a colony of bacteria.

3. The method of claim 1, wherein contacting a sample material with the first hydrogel-forming composition or second hydrogel-forming composition of the device comprises placing the sample in fluid communication with a nutrient to facilitate growth of an aerobic bacterium.

4. The method of claim 1, wherein incubating the inoculated culture device for a period of time comprises incubating the inoculated culture device for about 22 hours to about 26 hours, inclusive.

* * * * *